(12) United States Patent  
Holley

(10) Patent No.: US 9,358,396 B2
(45) Date of Patent: Jun. 7, 2016

(54) SYSTEMS AND METHODS FOR DELIVERING SUB-THRESHOLD THERAPY TO A PATIENT AT A PHYSIOLOGICAL MIDLINE

(71) Applicant: Boston Scientific Neuromodulation Corporation, Valencia, CA (US)

(72) Inventor: Justin Holley, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/528,533

(22) Filed: Oct. 30, 2014

(65) Prior Publication Data

US 2015/0127062 A1 May 7, 2015

Related U.S. Application Data

(60) Provisional application No. 61/898,908, filed on Nov. 1, 2013.

(51) Int. Cl.
*A61N 1/00* (2006.01)
*A61N 1/36* (2006.01)
(Continued)

(52) U.S. Cl.
CPC .......... *A61N 1/36185* (2013.01); *A61N 1/0551* (2013.01); *A61N 1/36071* (2013.01);
(Continued)

(58) Field of Classification Search
CPC ............ A61N 1/36021; A61N 1/3605; A61N 1/36071; A61N 1/36132; A61N 1/36135; A61N 1/36164
See application file for complete search history.

(56) References Cited

U.S. PATENT DOCUMENTS 5,938,690 A  8/1999 Law et al.
5,941,906 A  8/1999 Barreras, Sr. et al.
(Continued)

FOREIGN PATENT DOCUMENTS

CN  102512757 A  6/2012
WO  WO-2006029257 A2  3/2006
(Continued)

OTHER PUBLICATIONS

Kothandaraman. Sridhar, et al., "System and Method for Connecting Devices to a Neurostimulator", U.S. Appl. No. 61/694,695, filed Aug. 29, 2012.
(Continued)

*Primary Examiner* — Scott Getzow
(74) *Attorney, Agent, or Firm* — Schwegman Lundberg & Woessner, P.A.

(57) ABSTRACT

A method of operating an implantable neuromodulator coupled to an electrode array implanted adjacent tissue of a patient includes conveying electrical modulation energy to the tissue per a series of modulation parameter sets, thereby displacing the locus of the resulting electrical field laterally relative to the tissue, associating a plurality of different loci with the modulation parameter sets, causing the patient to perceive paresthesia, identifying a modulation parameter set as creating an electrical field having a locus disposed on a physiological midline of the patient based on the perceived paresthesia, deriving another modulation parameter set from the identified modulation parameter set, conveying electrical modulation energy to the patient per the other modulation parameter set, thereby creating an electrical field having a locus relative to the tissue that is the same as the locus of the electrical field associated with the identified modulation parameter set, without causing paresthesia.

20 Claims, 18 Drawing Sheets

(51) Int. Cl.
*A61N 1/05* (2006.01)
*A61N 1/372* (2006.01)

(52) U.S. Cl.
CPC ........ *A61N1/36132* (2013.01); *A61N 1/36164* (2013.01); *A61N 1/36171* (2013.01); *A61N 1/36175* (2013.01); *A61N 1/37247* (2013.01)

(56) References Cited

U.S. PATENT DOCUMENTS

| | | | |
|---|---|---|---|
| 6,516,227 | B1 | 2/2003 | Meadows et al. |
| 6,675,046 | B2 | 1/2004 | Holsheimer |
| 6,895,280 | B2 | 5/2005 | Meadows et al. |
| 6,993,384 | B2 | 1/2006 | Bradley et al. |
| 7,317,948 | B1 | 1/2008 | King et al. |
| 7,333,857 | B2 | 2/2008 | Campbell |
| 7,539,538 | B2 | 5/2009 | Parramon et al. |
| 7,650,184 | B2 | 1/2010 | Walter |
| 7,979,133 | B2 | 7/2011 | Feler et al. |
| 7,987,000 | B2 | 7/2011 | Moffitt et al. |
| 8,019,439 | B2 | 9/2011 | Kuzma et al. |
| 8,160,328 | B2 | 4/2012 | Goetz et al. |
| 8,180,129 | B2 | 5/2012 | Goetz et al. |
| 8,224,453 | B2 | 7/2012 | De Ridder |
| 8,255,057 | B2 | 8/2012 | Fang et al. |
| 8,355,797 | B2 | 1/2013 | Caparso et al. |
| 8,380,318 | B2 | 2/2013 | Kishawi et al. |
| 8,412,345 | B2 | 4/2013 | Moffitt |
| 8,437,857 | B2 | 5/2013 | Moffitt et al. |
| 8,455,716 | B2 | 6/2013 | Huang et al. |
| 8,504,147 | B2 | 8/2013 | Deem et al. |
| 8,615,300 | B2 | 12/2013 | Feler et al. |
| 8,649,874 | B2 | 2/2014 | Alataris et al. |
| 8,660,653 | B2 | 2/2014 | Kothandaraman |
| 8,670,831 | B2 | 3/2014 | Wacnik et al. |
| 8,676,329 | B2 | 3/2014 | Wacnik et al. |
| 8,676,331 | B2 | 3/2014 | Parker |
| 8,700,178 | B2 | 4/2014 | Anderson |
| 8,731,675 | B2 | 5/2014 | Ranu et al. |
| 8,751,009 | B2 | 6/2014 | Wacnik |
| 2003/0139781 | A1 | 7/2003 | Bradley et al. |
| 2004/0034394 | A1 | 2/2004 | Woods et al. |
| 2004/0098063 | A1 | 5/2004 | Goetz |
| 2004/0116978 | A1 | 6/2004 | Bradley |
| 2007/0150036 | A1 | 6/2007 | Anderson |
| 2008/0188909 | A1 | 8/2008 | Bradley |
| 2009/0196472 | A1 | 8/2009 | Goetz et al. |
| 2009/0198306 | A1 | 8/2009 | Goetz et al. |
| 2009/0204173 | A1 | 8/2009 | Fang et al. |
| 2009/0326608 | A1 | 12/2009 | Huynh et al. |
| 2010/0010566 | A1 | 1/2010 | Thacker et al. |
| 2010/0121409 | A1 | 5/2010 | Kothandaraman et al. |
| 2010/0249875 | A1 | 9/2010 | Kishawi et al. |
| 2010/0274312 | A1 | 10/2010 | Alataris et al. |
| 2010/0274314 | A1 | 10/2010 | Alataris et al. |
| 2010/0274315 | A1 | 10/2010 | Alataris et al. |
| 2010/0274317 | A1 | 10/2010 | Parker et al. |
| 2010/0274318 | A1 | 10/2010 | Walker et al. |
| 2010/0274326 | A1 | 10/2010 | Chitre et al. |
| 2010/0305660 | A1* | 12/2010 | Hegi et al. ........................ 607/60 |
| 2011/0106215 | A1* | 5/2011 | Moffitt ............................ 607/60 |
| 2011/0282414 | A1 | 11/2011 | Kothandaraman et al. |
| 2012/0059446 | A1 | 3/2012 | Wallace et al. |
| 2012/0083709 | A1 | 4/2012 | Parker et al. |
| 2012/0083857 | A1 | 4/2012 | Bradley |
| 2012/0253422 | A1 | 10/2012 | Thacker et al. |
| 2012/0265279 | A1 | 10/2012 | Zhu |
| 2012/0283797 | A1 | 11/2012 | De Ridder |
| 2012/0290041 | A1 | 11/2012 | Kim et al. |
| 2013/0066411 | A1 | 3/2013 | Thacker et al. |
| 2013/0116752 | A1 | 5/2013 | Parker et al. |
| 2013/0158630 | A1* | 6/2013 | Lee ................................ 607/59 |
| 2013/0261697 | A1* | 10/2013 | Parker ............................ 607/46 |
| 2013/0268021 | A1 | 10/2013 | Moffitt |
| 2013/0296975 | A1 | 11/2013 | Lee et al. |
| 2014/0081349 | A1 | 3/2014 | Lee et al. |
| 2014/0277267 | A1 | 9/2014 | Vansickle et al. |

FOREIGN PATENT DOCUMENTS

WO WO-2006135791 A2 12/2006
WO WO-2015066303 A1 5/2015

OTHER PUBLICATIONS

Lee, Dongchul, "Neurostimulation System for Defining a Generalized Ideal Multipole Configuration", U.S. Appl. No. 61/452,965, filed Mar. 15, 2011.
Rao, Prakash, et al. "Technique for Linking Electrodes Together During Programming of Neurostimulation System", U.S. Appl. No. 61/561,760, filed Nov. 18, 2011.
Vansickle, Dennis Allen, et al., "Neuromodulation System and Method for Transitioning Between Programming Modes", U.S. Appl. No. 14/214,752, filed Mar. 15, 2014.
Vansickle, Dennis Allen, "Systems and Methods for Delivering Sub-Threshold Therapy to a Patient", U.S. Appl. No. 61/801,917, filed Mar. 15, 2013.
"International Application Serial No. PCT/US2014/63119, International Search Report mailed Jan. 29, 2015", 5 pgs.
"International Application Serial No. PCT/US2014/63119, Written Opinion mailed Jan. 29, 2015", 6 pgs.

* cited by examiner

SYSTEMS AND METHODS FOR DELIVERING SUB-THRESHOLD THERAPY TO A PATIENT AT A PHYSIOLOGICAL MIDLINE

CLAIM OF PRIORITY

This application claims the benefit of priority under 35. U.S.C. §119(e) of U.S. Provisional Patent Application Ser. No. 61/898,908, filed on Nov. 1, 2013, which is herein incorporated by reference in its entirety.

FIELD OF THE INVENTION

The present inventions relate to tissue modulation systems, and more particularly, to programmable neuromodulation systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrodes carrying stimulation leads, which are implanted at the desired stimulation site, and an implantable neuromodulation device (e.g., an implantable pulse generator (IPG)) implanted remotely from the stimulation site, but coupled either directly to the neuromodulation lead(s) or indirectly to the neuromodulation lead(s) via a lead extension. The neuromodulation system may further comprise a handheld external control device (e.g., a remote control (RC)) to remotely instruct the neuromodulator to generate electrical stimulation pulses in accordance with selected stimulation parameters.

Implantable neuromodulation devices are active devices requiring energy for operation, and thus, the neuromodulation system oftentimes includes an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be stored in a rechargeable battery within the neuromodulation device, which can then be used to power the electronic componentry on-demand. Depending on the settings, the neuromodulation device may need to be recharged every 1-30 days.

Electrical stimulation energy may be delivered from the neuromodulation device to the electrodes in the form of an electrical pulsed waveform. Thus, stimulation energy may be controllably delivered to the electrodes to stimulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses provided through the electrode array. Each electrode configuration, along with the electrical pulse parameters, can be referred to as a "stimulation parameter set."

With some neuromodulation systems, and in particular, those with independently controlled current or voltage sources, the distribution of the current to the electrodes (including the case of the neuromodulation device, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulation device to generate electrical stimulation pulses in accordance with the selected stimulation parameters. Typically, the stimulation parameters programmed into the neuromodulation device can be adjusted by manipulating controls on the external control device to modify the electrical stimulation provided by the neuromodulation device system to the patient. Thus, in accordance with the stimulation parameters programmed by the external control device, electrical pulses can be delivered from the neuromodulation device to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neuromodulation device through a computerized programming system. This programming system can be a self-contained hardware/software system, or can be defined predominantly by software running on a standard personal computer (PC). The PC or custom hardware may actively control the characteristics of the electrical stimulation generated by the neuromodulation device to allow the optimum stimulation parameters to be determined based on patient feedback or other means and to subsequently program the neuromodulation device with the optimum stimulation parameter set or sets. The computerized programming system may be operated by a clinician attending the patient in several scenarios.

For example, in order to achieve an effective result from SCS, the lead or leads must be placed in a location, such that the electrical stimulation will cause paresthesia. The current understanding is that paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neuromodulation device to apply electrical stimulation to test placement of the leads and/or electrodes, thereby assuring that the leads and/or electrodes are implanted in effective locations within the patient. However, despite location of paresthesia in the location of the pain, not all SCS effectively treats pain. There, thus, remains a need for alternative SCS treatment locations on a patient's body.

Once the leads are correctly positioned, a fitting procedure, which may be referred to as a navigation session, may be performed using the computerized programming system to program the external control device, and if applicable the neuromodulation device, with a set of stimulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neuromodulation device (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Although alternative or artifactual sensations, known as paresthesia, are often appreciated by patients, patients sometimes report these sensations to be uncomfortable, and therefore, they can be considered an adverse side-effect to neuromodulation therapy in some cases. It has been shown that the delivery of sub-threshold electrical energy (e.g., high-rate pulsed electrical energy and/or low pulse width electrical energy) can be effective in providing neuromodulation therapy for chronic pain without causing paresthesia.

A patient's physiological midline is a line of electrical field positions (i.e., loci) on the patient's body where the effect of the stimulation (e.g., paresthesia) is felt symmetrically or equally on both sides of the patient's body. However, the physiological midline varies from patient to patient and does not necessarily coincide with the anatomic midline. Further, it is difficult to immediately determine if the sub-threshold neuromodulation therapy is delivered to the physiological midline of a patient, because there is a lack of paresthesia that may otherwise indicate that the electrical field is being delivered to the physiological midline of a patient. There, thus, remains a need to provide a neuromodulation system that is capable of delivering sub-threshold neuromodulation therapy to the physiological midline of a patient.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

SUMMARY OF THE INVENTION

Figure 1:
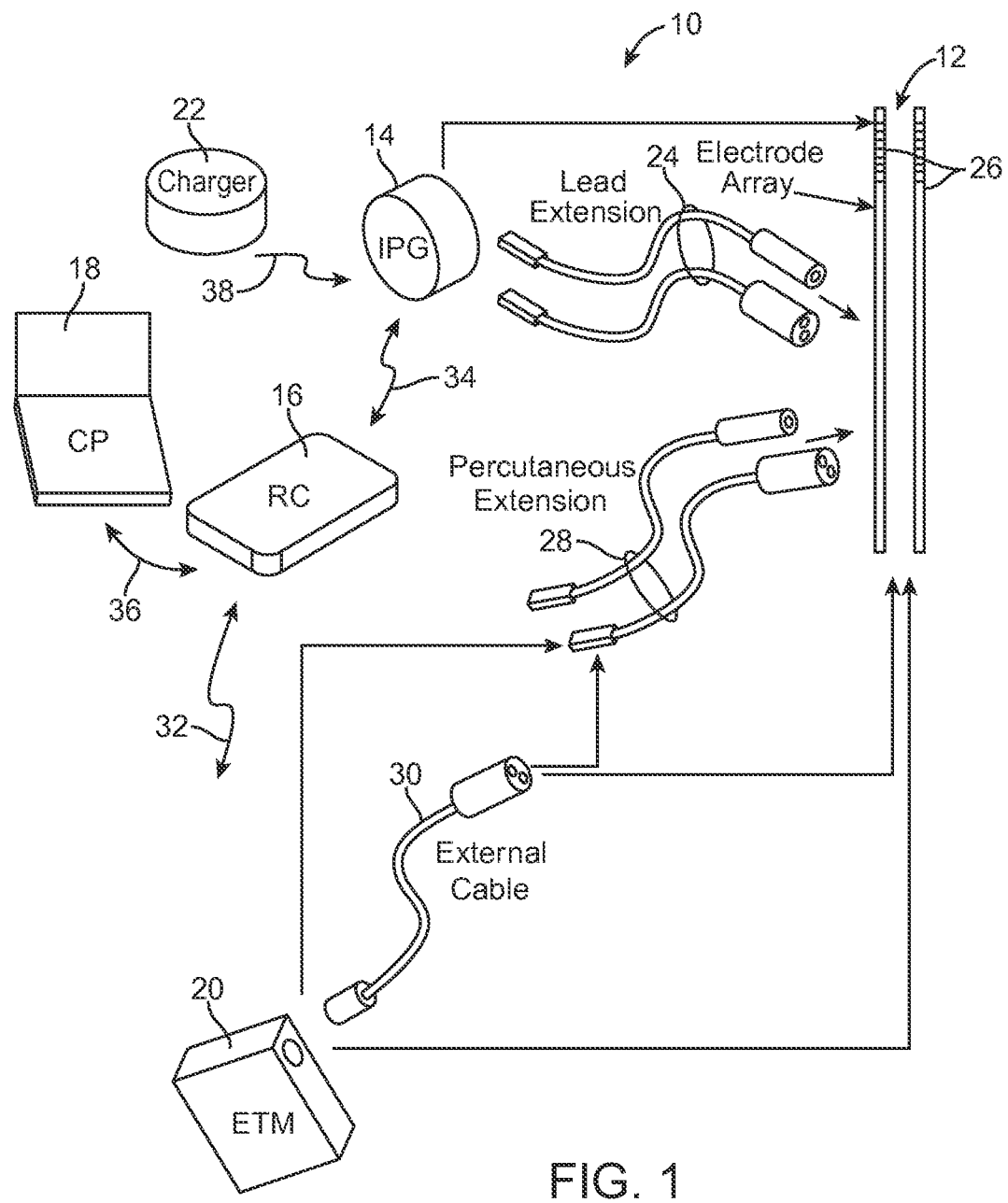
FIG. 1 is a plan view of a Spinal Cord Modulation (SCM) system constructed in accordance with one embodiment of the present inventions.

In accordance with a first aspect of the present inventions, a method of operating an implantable neuromodulator coupled to an electrode array implanted adjacent tissue (e.g., spinal cord tissue) of a patient having a medical condition is provided. The method comprises conveying electrical modulation energy to tissue of the patient in accordance with a series of modulation parameter sets, thereby gradually displacing the locus of the resulting electrical field laterally relative to the tissue. The method also comprises respectively associating a plurality of different loci of the resulting electrical field with the series of modulation parameter sets. The method further comprises causing the patient to perceive paresthesia in response to the conveyance of the electrical modulation energy to the tissue in accordance with at least one of the modulation parameter sets. Moreover, the method comprises identifying one of the at least one modulation parameter sets as creating an electrical field having a locus disposed on a physiological midline of the patient based on the perceived paresthesia. In addition, the method comprises deriving another modulation parameter set from the identified modulation parameter set. The method also comprises conveying electrical modulation energy to the tissue of the patient in accordance with the other modulation parameter set, thereby creating an electrical field having a locus relative to the tissue that is the same as the locus of the electrical field associated with the identified modulation parameter set, and without causing the patient to perceive paresthesia.

In one embodiment, the medical condition (e.g., chronic pain) affects a body region of the patient, and the electrical modulation energy conveyed to the tissue in accordance with the identified modulation parameter set causes the patient to perceive the paresthesia in the body region. The identified modulation parameter set and the other modulation parameter set may define different pulse rates (e.g., the identified modulation parameter set defines a pulse rate less than 1500 Hz, and the other modulation parameter set defines a pulse rate greater than 1500 Hz). The identified modulation parameter set and the other modulation parameter set may define different pulse widths (e.g., the identified modulation parameter set defines a pulse width greater than 100 μs, and the other modulation parameter set defines a pulse width less than 100 μs). The identified modulation parameter set may define an electrode combination (e.g., a fractionalized electrode combination or a multipolar electrode combination), and the other modulation parameter set may define the same electrode combination.

In another embodiment, the method also comprises displacing a virtual pole relative to the electrode array, and computing fractionalized electrode combinations that respectively emulate the displaced virtual pole. The series of modulation parameter sets may respectively define the fractionalized electrode combinations. The identified modulation parameter set may define a fractionalized electrode combination corresponding to one of the series of virtual poles, and the other modulation parameter set may define the same fractionalized electrode combination. The virtual pole may be laterally displaced across the electrode array.

In still another embodiment, the method also comprises programming the neuromodulator with the other modulation parameter set. The neuromodulator may be implanted within the patient. The method may also comprise displacing the locus of the resulting electrical field relative to the tissue in response to user input.

In accordance with a second aspect of the present inventions, a method of providing therapy to a patient using an implantable neuromodulator implanted within the patient is provided. The method comprises conveying electrical modulation energy to tissue of the patient to generate an electrical field having a locus relative to the tissue in a super-threshold mode, thereby causing the patient to perceive paresthesia. The method also comprises laterally steering the locus of the electrical field by modifying a fractionalized electrode combination while operating the neuromodulator in the super-threshold delivery mode and receiving feedback from the patient to determine a physiological midline. The method further comprises identifying a locus disposed on a physiological midline of the patient and a corresponding fractionalized electrode combination based on the perceived paresthesia. Moreover, the method comprises switching operation of the neuromodulator to a sub-threshold delivery mode, while maintaining corresponding fractionalized electrode combination. In addition, the method comprises delivering electrical modulation energy to the identified locus on the physiological midline of the patient in the sub-threshold delivery mode to provide sub-threshold therapy to the patient. The neuromodulator delivers electrical modulation energy to the patient when in the sub-threshold delivery mode that provides sub-threshold therapy to the patient.

In one embodiment, the method also comprises identifying another locus disposed on the physiological midline of the patient and another corresponding fractionalized electrode combination based on the perceived paresthesia, and delivering electrical modulation energy to the other identified locus on the physiological midline of the patient in the sub-threshold delivery mode to provide sub-threshold therapy to the patient. The method may also comprise identifying a plurality of loci disposed on the physiological midline of the patient and a plurality of corresponding fractionalized electrode combination based on the perceived paresthesia, fitting a curve to the plurality of loci disposed on the physiological midline, switching operation of the neuromodulator to the a sub-threshold delivery mode, and delivering electrical modulation energy to a point on the fitted curve of the patient in the sub-threshold delivery mode to provide sub-threshold therapy to the patient. The neuromodulator may deliver electrical modulation energy to the patient when in the sub-threshold delivery mode that provides sub-threshold therapy to the patient.

In another embodiment, the neuromodulator delivers the electrical modulation energy at a pulse rate less than 1500 Hz when in the super-threshold delivery mode, and delivers the electrical modulation energy at a pulse rate greater than 1500 Hz when in the sub-threshold delivery mode. The neuromodulator may deliver the electrical modulation energy at a pulse rate less than 500 Hz when in the super-threshold delivery mode, and delivers the electrical modulation energy at a pulse rate greater than 2500 Hz when in the sub-threshold delivery mode. The neuromodulator may deliver the electrical modulation energy at a pulse width greater than 100 μs when in the super-threshold delivery mode, and delivers the electrical modulation energy at a pulse width less than 100 μs when in the sub-threshold delivery mode. The neuromodulator may deliver the electrical modulation energy at a pulse width greater than 200 μs when in the super-threshold delivery mode, and delivers the electrical modulation energy at a pulse width less than 50 μs when in the sub-threshold delivery mode. The patient may suffer from chronic pain in a body region, and the paresthesia may be perceived by the patient in the body region when the modulation energy is delivered to the patient when the neuromodulator is in the super-threshold delivery mode.

In accordance with a third aspect of the present inventions, an external control device for programming an implantable neuromodulator coupled to an electrode array is provided. The external control device comprises a user interface including a programming selection control element configured for allowing a user to select a super-threshold programming mode having a first limit on a modulation parameter and a sub-threshold programming mode having a second limit on the modulation parameter different from the first limit. The external control device also comprises controller/processor circuitry configured for defining a series of modulation parameter sets during the programming of the neuromodulator in the super-threshold programming mode, and instructing the neuromodulator to convey electrical energy to the electrode array in accordance with the series of modulation parameter sets in a manner that displaces a locus of a resulting electrical field relative to the electrode array. The controller/processor circuitry is also configured for automatically identifying one of the series of modulation parameter sets as creating an electrical field having a locus disposed on a physiological midline of the patient.

In one embodiment, the controller/processor circuitry, in response to the actuation of the programming selection control element, is configured for deriving another modulation parameter set from the identified modulation parameter set of the series of modulation parameter sets, and instructing the neuromodulator to convey electrical energy to the electrode array in accordance with the other modulation parameter set during the programming of the neuromodulation to device in the sub-threshold programming mode. The controller/processor circuitry may be configured for deriving the other modulation parameter set in a manner that causes an electrical field resulting from the conveyance of the electrical energy to the electrode array in accordance with the other modulation parameter set to have a locus that is the same as the locus of the electrical field resulting from the conveyance of the electrical energy to the electrode array in accordance with the identified modulation parameter set.

In another embodiment, the modulation parameter is a pulse rate, the first limit is an upper limit value less than 1500 Hz, and the second limit is a lower limit value greater than 1500 Hz. The modulation parameter may be a pulse width, the first limit may be a lower limit value greater than 100 µs, and the second limit may be an upper limit value less than 100 µs. The sub-threshold programming mode may be a semi-automated programming mode.

In still another embodiment, the controller/processor circuitry is configured for automatically defining a virtual multipole relative to the electrode array when programming the neuromodulator in the super-threshold programming mode, and computing modulation parameters for the electrode array that emulate the virtual multipole, wherein a first modulation parameter set includes the computed modulation parameters. The controller/processor circuitry may also be configured for panning the virtual multipole laterally across the electrode array. The external control device may also comprise telemetry circuitry, wherein the controller/processor circuitry is configured for programming the neuromodulator via the telemetry circuitry. The external control device may further comprise a housing containing the user interface and the controller/processor circuitry.

Other and further aspects and features of the invention will be evident from reading the following detailed description of the preferred embodiments, which are intended to illustrate, not limit, the invention.

DETAILED DESCRIPTION OF THE EMBODIMENTS

Turning first to FIG. 1, an exemplary SCM system 10 generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one, as long as the number of electrodes 26 is greater than two (including the IPG case) to allow for lateral steering of the current. Alternatively, a surgical paddle lead can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETM 20. For purposes of brevity, the details of the ETM 20 will not be described herein. Details of exemplary embodiments of ETM are disclosed in U.S. Pat. No. 6,895,280, which is expressly incorporated herein by reference.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the external charger 22 will not be described herein. Details of exemplary embodiments of the external charger are disclosed in U.S. Pat. No. 6,895,280, which is expressly incorporated herein by reference.

Figure 2:
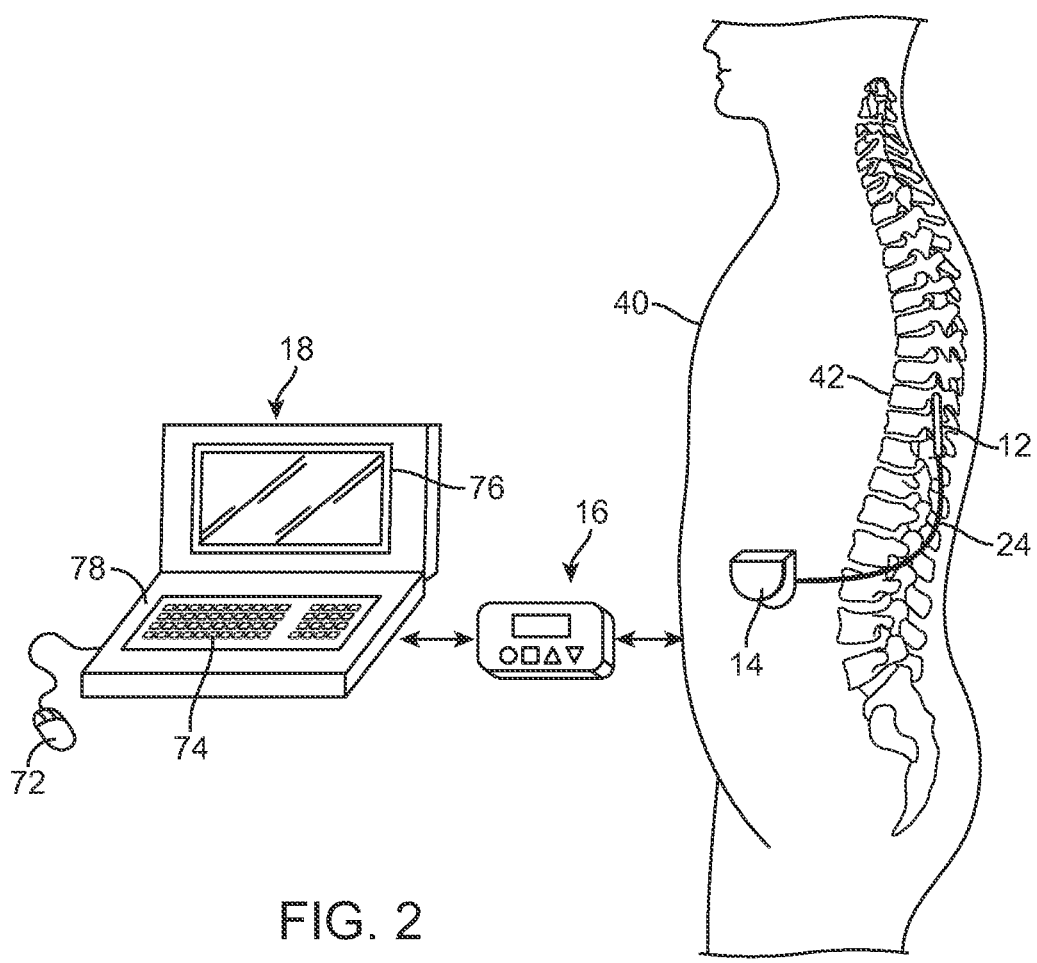
FIG. 2 is a plan view of the SCM system of FIG. 1 in use with a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be stimulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As shown in FIG. 2, the CP 18 communicates with the IPG 14 via the RC 16.

Figure 3:
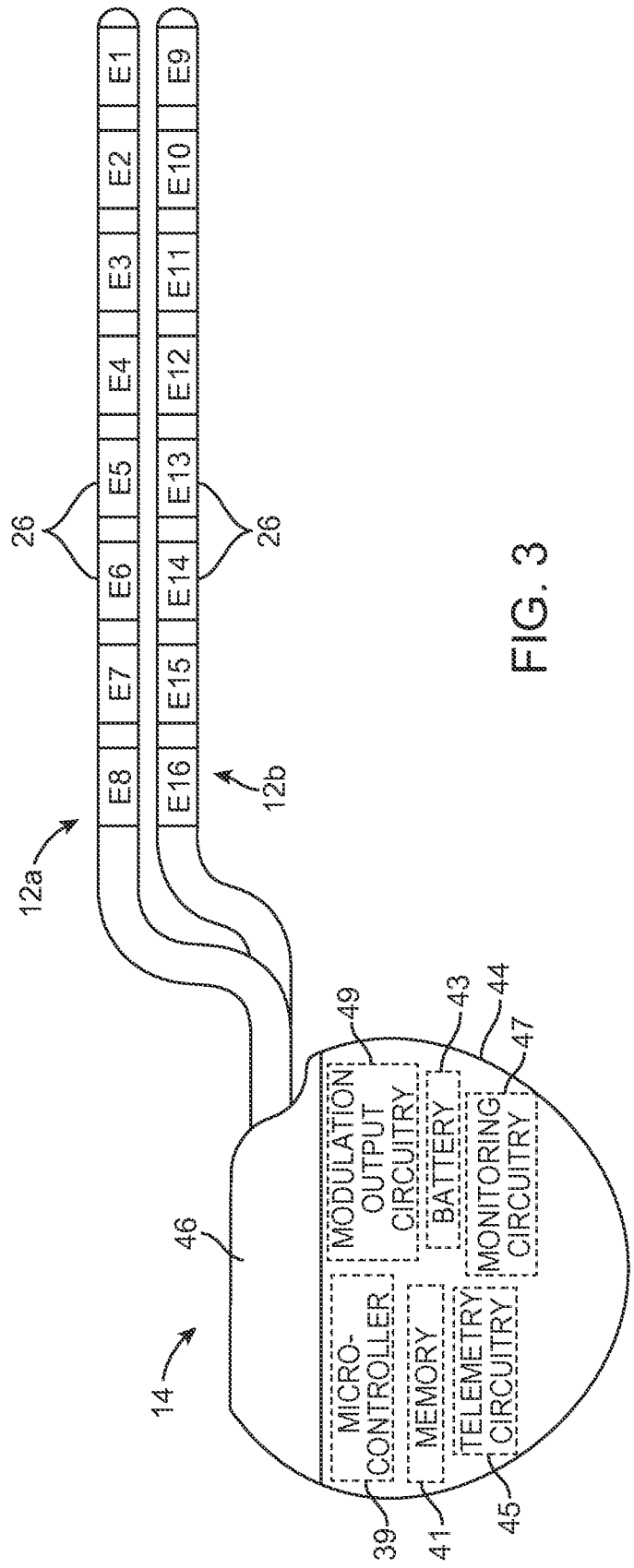
FIG. 3 is a profile view of an implantable pulse generator (IPG) and percutaneous leads used in the SCM system of FIG. 1.

Referring now to FIG. 3, the external features of the neuromodulation leads 12 and the IPG 14 will be briefly described. One of the neuromodulation leads 12*a* has eight electrodes 26 (labeled E1-E8), and the other neuromodulation lead 12*b* has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 comprises electronic components, such as a controller/processor (e.g., a microcontroller) 39, memory 41, a battery 43, telemetry circuitry 45, monitoring circuitry 47, modulation output circuitry 49, and other suitable components known to those skilled in the art. The microcontroller 39 executes a suitable program stored in memory 41, for directing and controlling the neuromodulation performed by IPG 14. Telemetry circuitry 45, including an antenna (not shown), is configured for receiving programming data (e.g., the operating program and/or modulation parameters) from the RC 16 and/or CP 18 in an appropriate modulated carrier signal, which the programming data is then stored in the memory (not shown). The telemetry circuitry 45 is also configured for transmitting status data to the RC 16 and/or CP 18 in an appropriate modulated carrier signal. The battery 43, which may be a rechargeable lithium-ion or lithium-ion polymer battery, provides operating power to IPG 14. The monitoring circuitry 47 is configured for monitoring the present capacity level of the battery 43.

The modulation output circuitry 49 provides electrical modulation energy in the form of a pulsed electrical waveform to the electrodes 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the modulation on duration X and modulation off duration Y).

Electrical modulation will occur between a plurality of activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12*a* may be activated as an anode at the same time that electrode E11 on the second lead 12*b* is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12*a* may be activated as anodes at the same time that electrode E12 on the second lead 12*b* is activated as a cathode. Such multipolar modulation facilitates lateral steering and fractionalization of current.

Any of the electrodes E1-E16 and case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (sourcing current), negative (sinking current), or off (no current) polarity in any of the k timing channels.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other neuromodulators that may be used with the invention include neuromodulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCM system 10 may alternatively utilize an implantable receiver-stimulator (not shown) connected to the neuromodulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-modulator. The implanted receiver-modulator receives the signal and generates the modulation in accordance with the control signals.

The IPG 14 may be operated in one of a super-threshold delivery mode and a sub-threshold delivery mode. While in the super-threshold delivery mode, the IPG 14 is configured for delivering electrical modulation energy that provides super-threshold therapy to the patient (in this case, causes the patient to perceive paresthesia). While in the sub-threshold delivery mode, the IPG 14 is configured for delivering electrical modulation energy that provides sub-threshold therapy to the patient (in this case, does not cause the patient to perceive paresthesia). Further details discussing modulation phases and delivery modes are described more fully in U.S. Provisional Patent Application Ser. No. 61/801,917, entitled "Systems and Methods for Delivering Sub-Threshold Therapy to a Patient," which is expressly incorporated herein by reference.

As briefly discussed above, the CP 18 greatly simplifies the programming of multiple electrode configurations, allowing the user (e.g., the physician or clinician) to readily determine the desired modulation parameters to be programmed into the IPG 14, as well as the RC 16. Thus, modification of the modulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum modulation parameters to be determined based on patient feedback and for subsequently programming the IPG 14 with the optimum modulation parameter.

To allow the user to perform these functions, the CP 18 includes a user input device (e.g., a mouse 72 and a keyboard 74), and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc., can be used to manipulate graphical objects on the display screen 76. In alternative embodiments, the display screen 76 takes the form of a digitizer touch screen, which may either passive or active. If passive, the display screen 76 includes detection circuitry (not shown) that recognizes pressure or a change in an electrical current when a passive device, such as a finger or non-electronic stylus, contacts the screen. If active, the display screen 76 includes detection circuitry that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked. Further details discussing the use of a digitizer screen for programming are set forth in U.S. Provisional Patent Application Ser. No. 61/561,760, entitled "Technique for Linking Electrodes Together during Programming of Neurostimulation System," which is expressly incorporated herein by reference.

Figure 4:
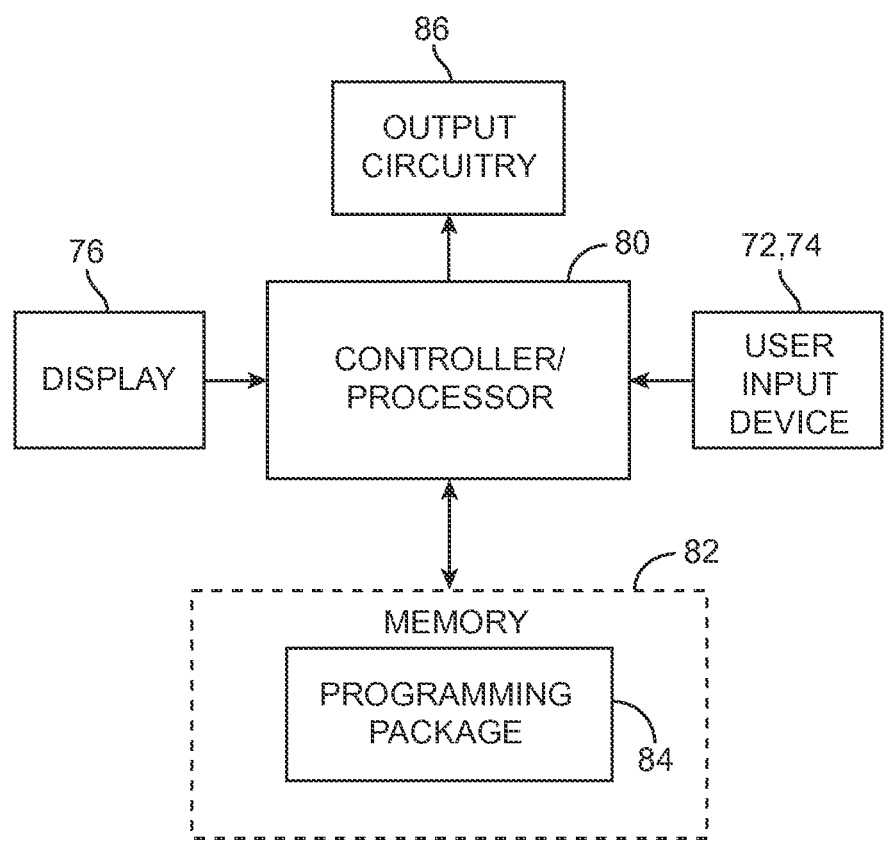
FIG. 4 is a block diagram of the internal components of a clinician's programmer (CP) used in the SCM system of FIG. 1.

As shown in FIG. 4, the CP 18 includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes an output circuitry 86 for downloading modulation parameters to the IPG 14 and RC 16 and for uploading modulation parameters already stored in the memory 66 of the RC 16 or memory of the IPG 14. In addition, the CP 18 further includes a user input device 88 (such as the mouse 72 or keyboard 74) to provide user commands. Notably, while the controller/processor 80 is shown in FIG. 4 as a single device, the processing functions and controlling functions can be performed by a separate controller and processor 64. Thus, it can be appreciated that the controlling functions described below as being performed by the CP 18 can be performed by a controller, and the processing functions described below as being performed by the CP 18 can be performed by the processor 64.

Execution of the programming package 84 by the controller/processor 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads 12, and select and program the IPG 14 with modulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Modulation energy Among Multiple Neuromodulation Electrodes," which are expressly incorporated herein by reference. Execution of the programming package 84 provides a user interface that conveniently allows a user to program the IPG 14.

Figure 5A:
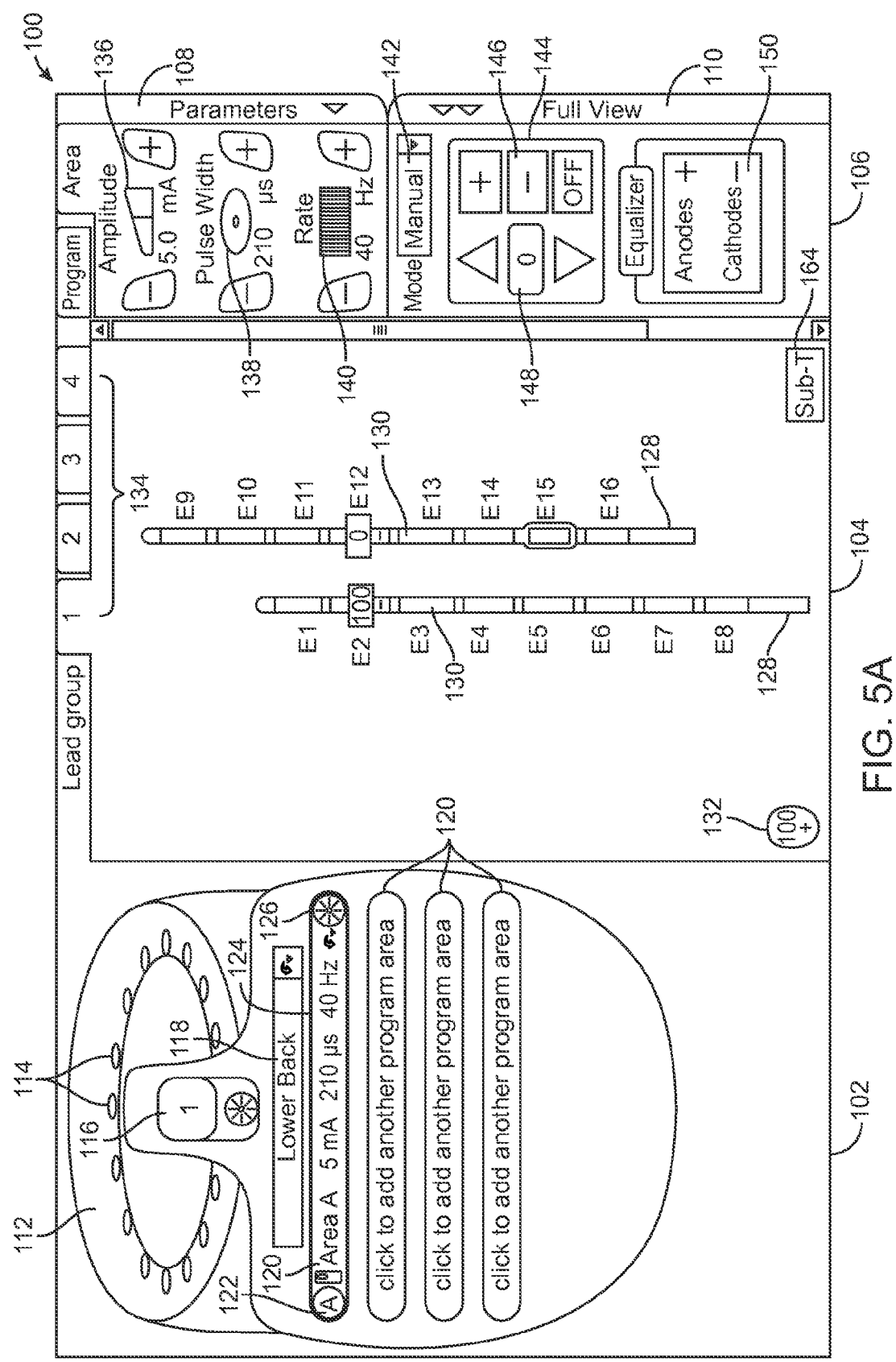
FIGS. 5A-5E are plan views of a user interface of the CP of FIG. 4 for programming the IPG of FIG. 3 in a manual programming mode.

Referring first to FIG. 5A, a graphical user interface (GUI) 100 that can be generated by the CP 18 to allow a user to program the IPG 14 will be described. In the illustrated embodiment, the GUI 100 comprises three panels: a program selection panel 102, a lead display panel 104, and a modulation parameter adjustment panel 106. Some embodiments of the GUI 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about modulation programs and coverage areas that have been, or may be, defined for the IPG 14. In particular, the program selection panel 102 includes a carousel 112 on which a plurality of modulation programs 114 (in this case, up to sixteen) may be displayed and selected. The program selection panel 102 further includes a selected program status field 116 indicating the number of the modulation program 114 that is currently selected (any number from "1" to "16"). In the illustrated embodiment, program 1 is the only one currently selected, as indicated by the number "1" in the field 116. The program selection panel 102 further comprises a name field 118 in which a user may associate a unique name to the currently selected modulation program 114. In the illustrated embodiment, currently selected program 1 has been called "lower back," thereby identifying program 1 as being the modulation program 114 designed to provide therapy for lower back pain.

The program selection panel 102 further comprises a plurality of coverage areas 120 (in this case, up to four) with which a plurality of modulation parameter sets can respectively be associated to create the currently selected modulation program 114 (in this case, program 1). Each coverage area 120 that has been defined includes a designation field 122 (one of letters "A"-"D"), and an electrical pulse parameter field 124 displaying the electrical pulse parameters, and specifically, the pulse amplitude, pulse width, and pulse rate, of the modulation parameter set associated with the that coverage area. In this example, only coverage area A is defined for program 1, as indicated by the "A" in the designation field 122. The electrical pulse parameter field 124 indicates that a pulse amplitude of 5 mA, a pulse width of 210 µs, and a pulse rate of 40 Hz has been associated with coverage area A.

Each of the defined coverage areas 120 also includes a selection icon 126 that can be alternately actuated to activate or deactivate the respective coverage area 120. When a coverage area is activated, an electrical pulse train is delivered from the IPG 14 to the electrode array 26 in accordance with the modulation parameter set associated with that coverage area. Notably, multiple ones of the coverage areas 120 can be simultaneously activated by actuating the selection icons 126 for the respective coverage areas. In this case, multiple electrical pulse trains are concurrently delivered from the IPG 14 to the electrode array 26 during timing channels in an interleaved fashion in accordance with the respective modulation parameter sets associated with the coverage areas 120. Thus, each coverage area 120 corresponds to a timing channel.

To the extent that any of the coverage areas 120 have not been defined (in this case, three have not been defined), they include text "click to add another program area"), indicating that any of these remaining coverage areas 120 can be selected for association with a modulation parameter set. Once selected, the coverage area 120 will be populated with the designation field 122, electrical pulse parameter field 124, and selection icon 126.

The lead display panel 104 includes graphical leads 128, which are illustrated with eight graphical electrodes 130 each (labeled electrodes E1-E8 for the first lead 128 and electrodes E9-E16 for second lead 128). The lead display panel 104 also includes a graphical case 132 representing the case 44 of the IPG 14. The lead display panel 104 further includes lead group selection tabs 134 (in this case, four), any of which can be actuated to select one of four groups of graphical leads 128. In this case, the first lead group selection tab 134 has been actuated, thereby displaying the two graphical leads 128 in their defined orientation. In the case where additional leads 12 are implanted within the patient, they can be associated with additional lead groups.

The parameters adjustment panel 106 also includes a pulse amplitude adjustment control 136 (expressed in milliamperes (mA)), a pulse width adjustment control 138 (expressed in microseconds (µs)), and a pulse rate adjustment control 140 (expressed in Hertz (Hz)), which are displayed and actuatable in all the programming modes. Each of the controls 136-140 includes a first arrow that can be actuated to decrease the value of the respective modulation parameter and a second arrow that can be actuated to increase the value of the respective modulation parameter. Each of the controls 136-140 also includes a display area for displaying the currently selected parameter. In response to the adjustment of any of electrical pulse parameters via manipulation of the graphical controls in the parameter adjustment panel 106, the controller/processor 80 generates a corresponding modulation parameter set (with a new pulse amplitude, new pulse width, or new pulse rate) and transmits it to the IPG 14 via the telemetry circuitry 86 for use in delivering the modulation energy to the electrodes 26.

The parameter adjustment panel 106 includes a pull-down programming mode field 142 that allows the user to switch between a manual programming mode and an electronic trolling programming mode. Each of these programming modes allows a user to define a modulation parameter set for the currently selected coverage area 120 of the currently selected program 114 via manipulation of graphical controls in the parameter adjustment panel 106 described above, as well as the various graphical controls described below. In the illustrated embodiment, when switching between programming modes via actuation of the programming mode field 142, the last electrode configuration with which the IPG 14 was programmed in the previous programming mode is converted into another electrode configuration, which is used as the first electrode configuration with which the IPG 14 is programmed in the subsequent programming mode.

The electronic trolling programming mode is designed to allow a user to determine one or more efficacious modulation parameter sets for providing super-threshold therapy to the patient. In particular, the electronic trolling programming mode is designed to quickly sweep the electrode array using a limited number of electrode configurations to gradually steer an electrical field relative to the modulation leads until the targeted stimulation site is located. The electronic trolling mode relies on immediate feedback from the patient in response to the sensation of paresthesia relative to the region of the body in which the patient experiences pain.

Using the manual programming mode or the electronic trolling programming mode, a user can pan the locus of an electrical field laterally across an array of electrodes 26, and therefore across the spinal cord of the patient into which the array is implanted. The amount of displacement relative to the anatomic midline of the patient depends on fractionalization of the current, the placement of the leads 12 relative to the anatomy (e.g., spinal cord), and the unique physiology of the patient. By changing the fractionalization of the current, the locus of the resulting electrical field can be panned laterally from one side of the patient's anatomic midline to the other. Using patient feedback regarding the effect of the electrical field (e.g., paresthesia) while laterally panning the electrical field at an axial or vertebral level, the physiological midline at that axial level can be identified in terms of current fractionalization for a given array of electrodes 26 implanted in a particular patient.

An exemplary method for delivery modulation energy at a patient's physiological midline begins with implanting an array of electrodes 26 on one or more leads 12 and an IPG 14 in the patient. As shown in FIG. 2, the leads 12 are connected to the IPG 14 by lead extensions 24, which are also implanted in the patent. The IPG 14 is connected to the CP 18 as described above.

Using the CP 18, a user (e.g., a physician) instructs the IPG 14 to generate a modulation signal resulting in an electrical field having a locus. The user can use either the manual programming mode or the electronic trolling programming mode (both described in examples below) of the CP 18 to set various modulation parameters. The electrical field locus can be displaced by fractionalizing the cathodic current across the array of electrodes 26. Other modulation parameters (e.g., amplitude, frequency, duty cycle, pulse width, etc.) are adjusted to achieve super-threshold stimulation (i.e., stimulation that produces paresthesia in the patient).

Significantly, the physiological midline can be identified by eliciting patient feedback while incrementally panning the electrical laterally at a particular vertebral (i.e., axial) level. After identifying the physiological midline at a particular vertebral level, the lateral panning process can be repeated at a different vertebral level to identify the physiological midline at the new vertebral level.

The initial modulation signal sets the locus of the resulting electrical field and paresthesia at a particular axial level and preferably to one lateral extreme of the array of electrodes 26 (e.g., the far left side of the array). The user can then pan the electrical field locus laterally across the array of electrodes 26 by adjusting the modulation parameters using either the manual or electronic trolling programming modes of the CP 18. The user determines the rate of locus panning by adjusting the rate at which the modulation parameters are changed at the CP 18. The user laterally pans the electronic field locus to the opposite side of the array of electrodes 26 and across the patient's anatomic midline.

While the locus of the electrical field is panned laterally across the array of electrodes 26 using either of the manual or electronic trolling programming modes, the patient indicates when paresthesia of equal intensity is felt on both sides of the patient's body by providing voluntary feedback. The voluntary feedback may include oral indication, depression of a button, and/or interaction with a computer user interface. When the patient provides the voluntary feedback indicating equal intensity of paresthesia, the panning locus is, by definition, on the physiological midline of the patient. The CP 18 notes the physiological midline location by storing the fractionalized current that generated the electrical field with a locus on the physiological midline. The locus is panned at a speed such that the patient can accurately identify the physiological midline.

After identifying the physiological midline at a particular axial level as described above, the locus of the electrical field can be panned axially up or down to identify the physiological midline at another axial level, using the method described above. For example, the electrical field locus can be moved axially downward by directing the cathodic current to the next set of electrodes 26 in an axially downward direction in the array of electrodes 26. This process can be repeated at a plurality of axial levels, for instance at each vertebral level from C1 to S5, to identify a series of points along the physiological midline. Those identified points can be interpolated to estimate the location of the physiological midline in two dimensions.

Alternatively, the CP 18 or the IPG 14 can be programmed to slowly and systematically pan the electronic field locus laterally across the array of electrodes 26. For instance, the CP 18 can be programmed to generate an initial modulation signal at the upper left corner of the array of electrodes 26. The electrical field locus is then laterally and slowly panned to the extreme right side of the array at that axial level in a semi-automatic manner. When the patient provides feedback identifying the physiological midline at the first axial level, the CP 18 generates a signal at the extreme left side of a second axial level and laterally and slowly pans the electrical field locus to the extreme right side of the second axial level. If a patient cannot identify the physiological midline during a first "pass" at an axial level, the CP 18 generates signals to laterally pan the electrical field locus a second time at that axial level. The process is repeated until the physiological midline is identified at a desired series of axial levels (can be one axial level).

After the physiological midline is identified at one or more axial levels, the user selects a user interface object on the CP 18 to cause the IPG 14 to deliver sub-threshold signals (i.e., signals that do not result in paresthesia) to loci along the physiological midline of the patient. The CP 18 or the IPG 14 modifies the modulation parameters previously defined during the manual or electronic trolling programming modes to predetermined values that ensure sub-threshold modulation, while maintaining the position of each electrical field locus.

As shown in FIGS. 5A-5D, the manual programming mode has been selected. In the manual programming mode, each of the electrodes 130 of the graphical leads 128, as well as the graphical case 132, may be individually selected, allowing the clinician to set the polarity (cathode or anode) and the magnitude of the current (percentage) allocated to that electrode 130, 132 using graphical controls located in an amplitude/polarity area 144 of the parameter adjustment panel 106. Electrode E15 is shown as being selected to allow the user to subsequently allocate the polarity and fractionalized electrical current to it via the graphical controls located in the amplitude/polarity area 144.

In particular, a graphical polarity control 146 located in the amplitude/polarity area 144 includes a "+" icon, a "−" icon, and an "OFF" icon, which can be respectively actuated to toggle the selected electrode 130, 132 between a positive polarization (anode), a negative polarization (cathode), and an off-state. An amplitude control 148 in the amplitude/polarity area 144 includes an arrow that can be actuated to decrease the magnitude of the fractionalized current of the selected electrode 130, 132, and an arrow that can be actuated to increase the magnitude of the fractionalized current of the selected electrode 130, 132. The amplitude control 148 also includes a display area that indicates the adjusted magnitude of the fractionalized current for the selected electrode 134. The amplitude control 148 is preferably disabled if no electrode is visible and selected in the lead display panel 104. In response to the adjustment of fractionalized electrode combination via manipulation of the graphical controls in the amplitude/polarity area 144, the controller/processor 80 generates a corresponding modulation parameter set (with a new fractionalized electrode combination) and transmits it to the IPG 14 via the telemetry circuitry 86 for use in delivering the modulation energy to the electrodes 26.

In the embodiment illustrated in FIG. 5A, the graphical case 132 representing the case 44 of the IPG 14 has been selected as the anode to which 100% of the anodic current has been allocated, and electrode E2 has been selected as the cathode to which 100% of the cathodic current has been allocated. This particular fractionalization of the cathodic current creates an electrical field having a locus that is asymmetric with respect to the location of the two leads 12, represented by graphical leads 128 in the lead display panel 104. In this instance, the locus will be offset to the left side of the array of electrodes 26. The locus of the electrical field may also be displaced laterally relative to the anatomic midline of the patient depending on the relative location of the array of electrodes 26 and the spine of the patient into which the array is implanted.

The electrical field locus can be panned from the left side of the array of electrodes 26 to the right side, by adjusting the fractionalization of the cathodic current using the manual programming mode to gradually increase the percentage of the cathodic current allocated to E12 on the right side of the array of electrodes 26. Similarly, the electrical field locus can be panned leftward by increasing the percentage of the cathodic current allocated to electrode E2. Using this set of electrodes, the electrical field locus is displaced to its extreme left by setting the percentage of the cathodic current allocated to electrode E2 to 100% (as shown in FIG. 5A), and displaced to its extreme right by setting electrode E12 to 100% (as shown in FIG. 5E).

Figure 5B:
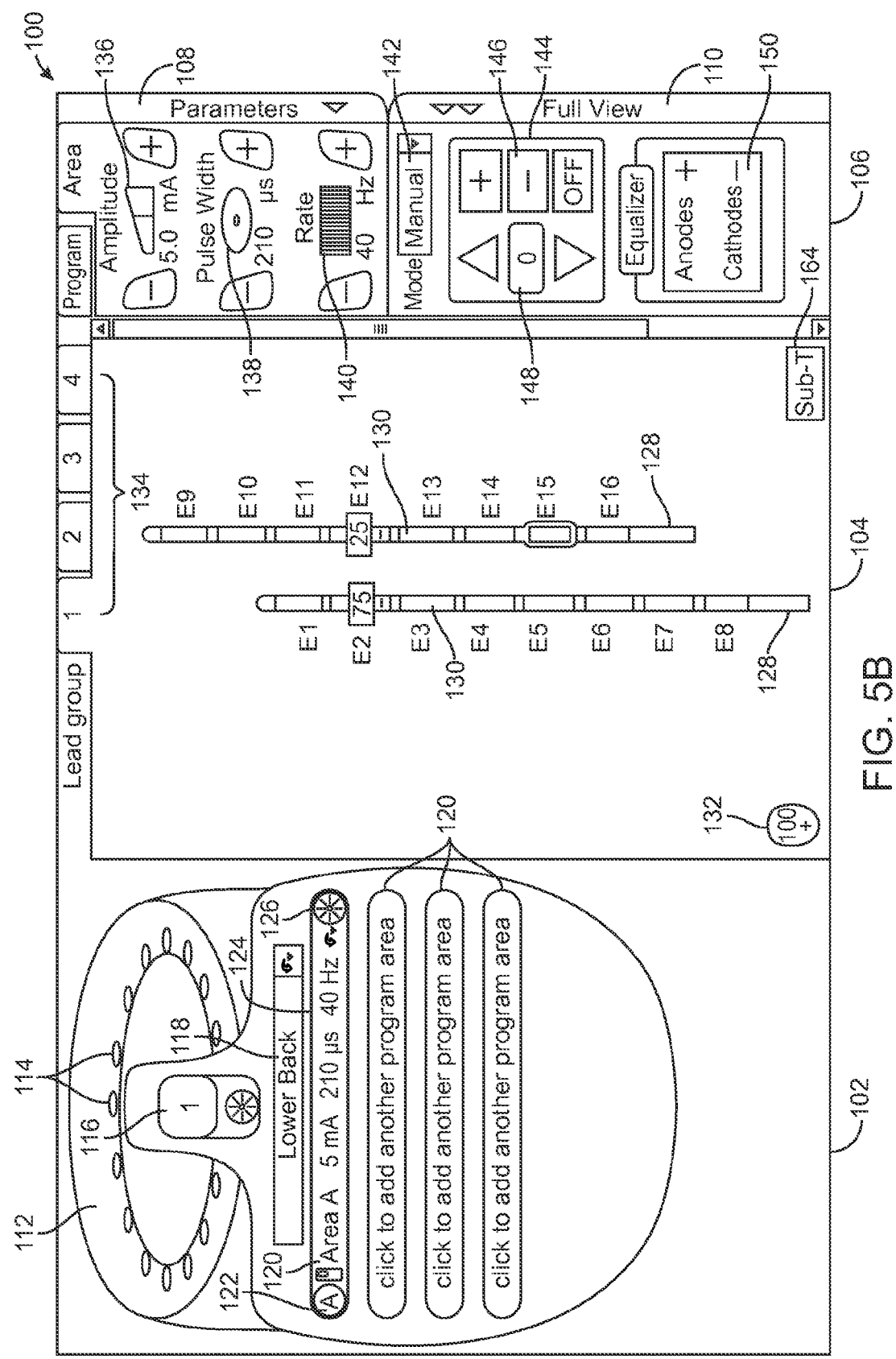
Figure 5C:
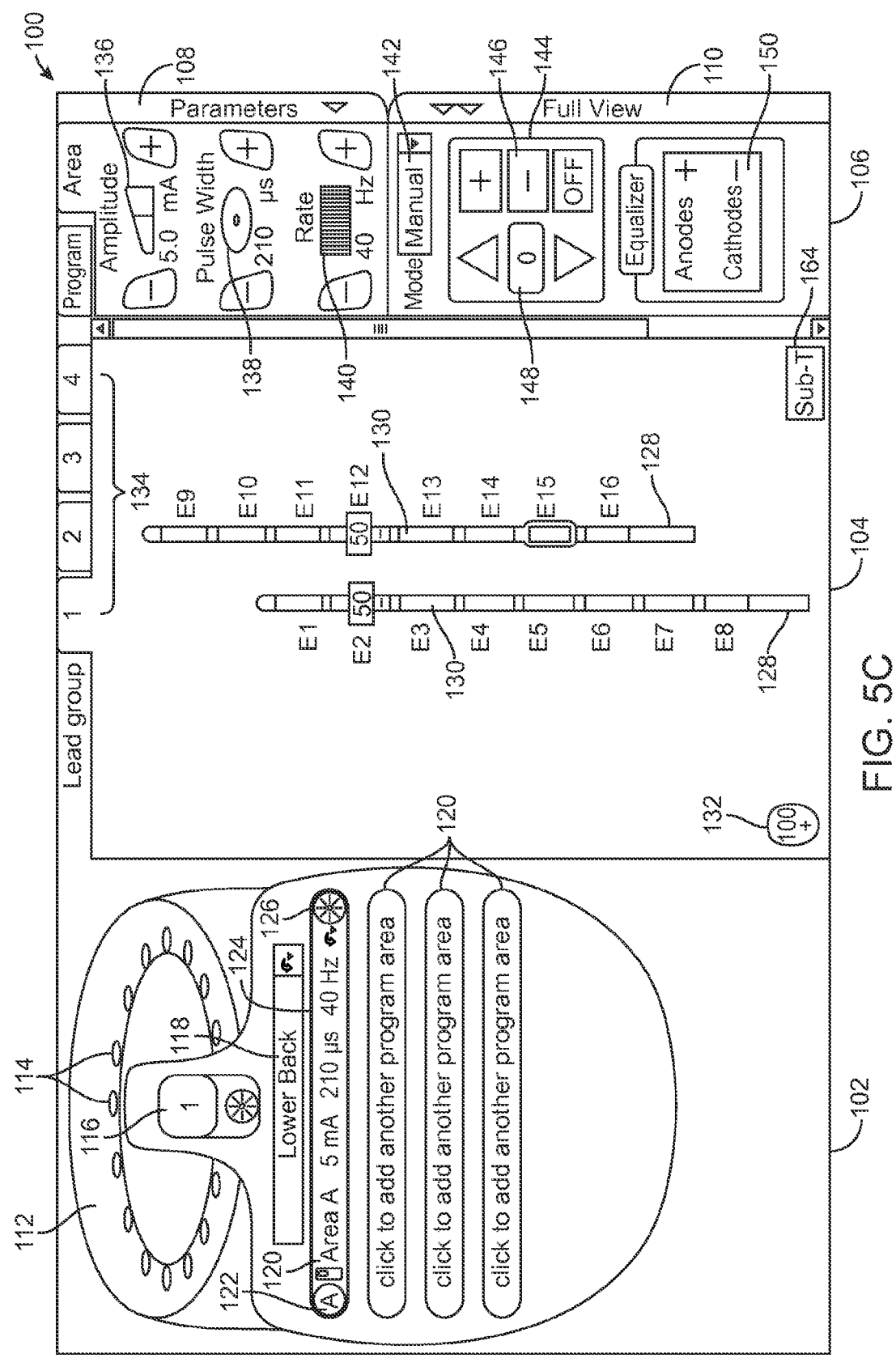
Figure 5D:
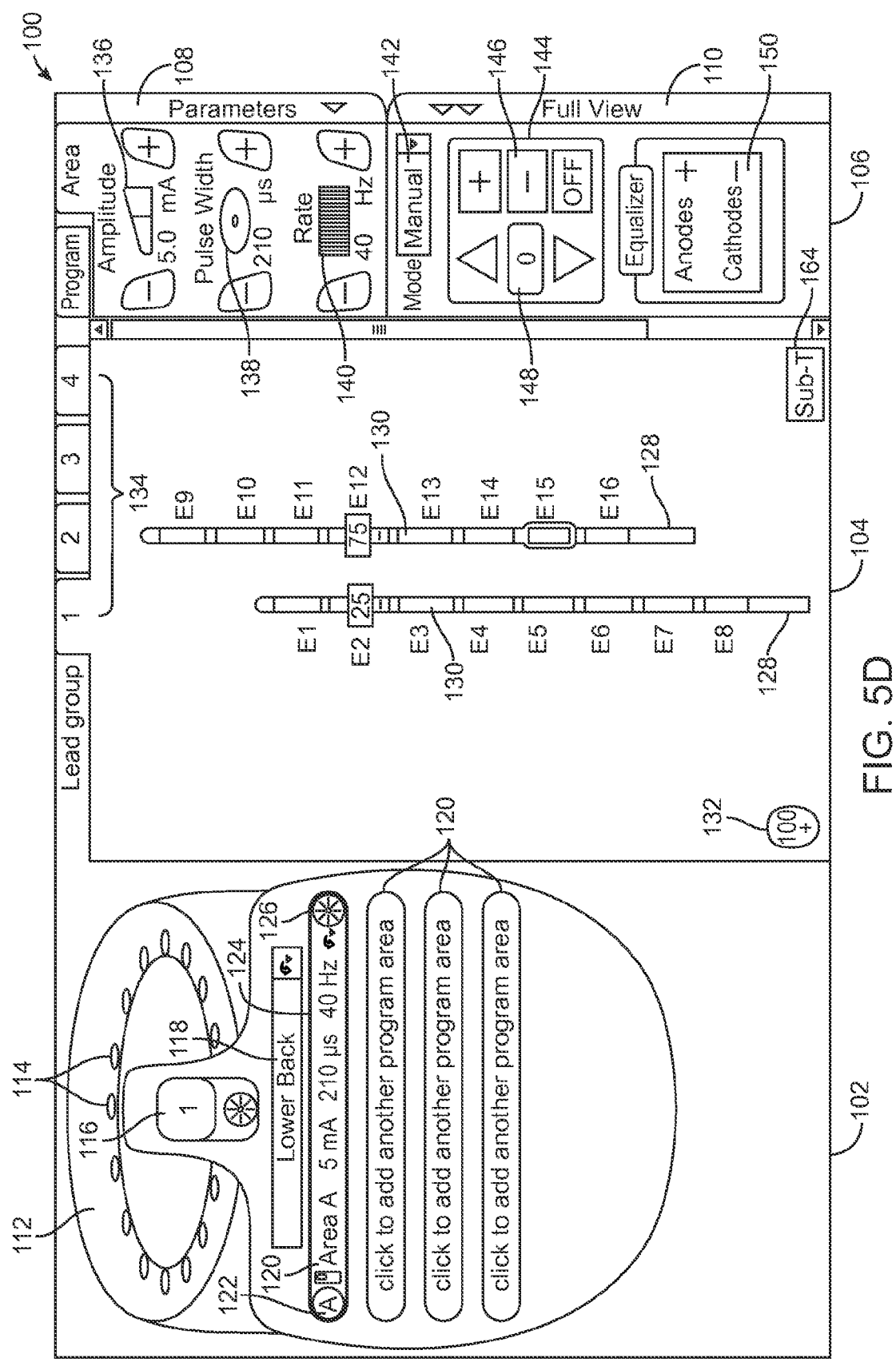
Figure 5E:
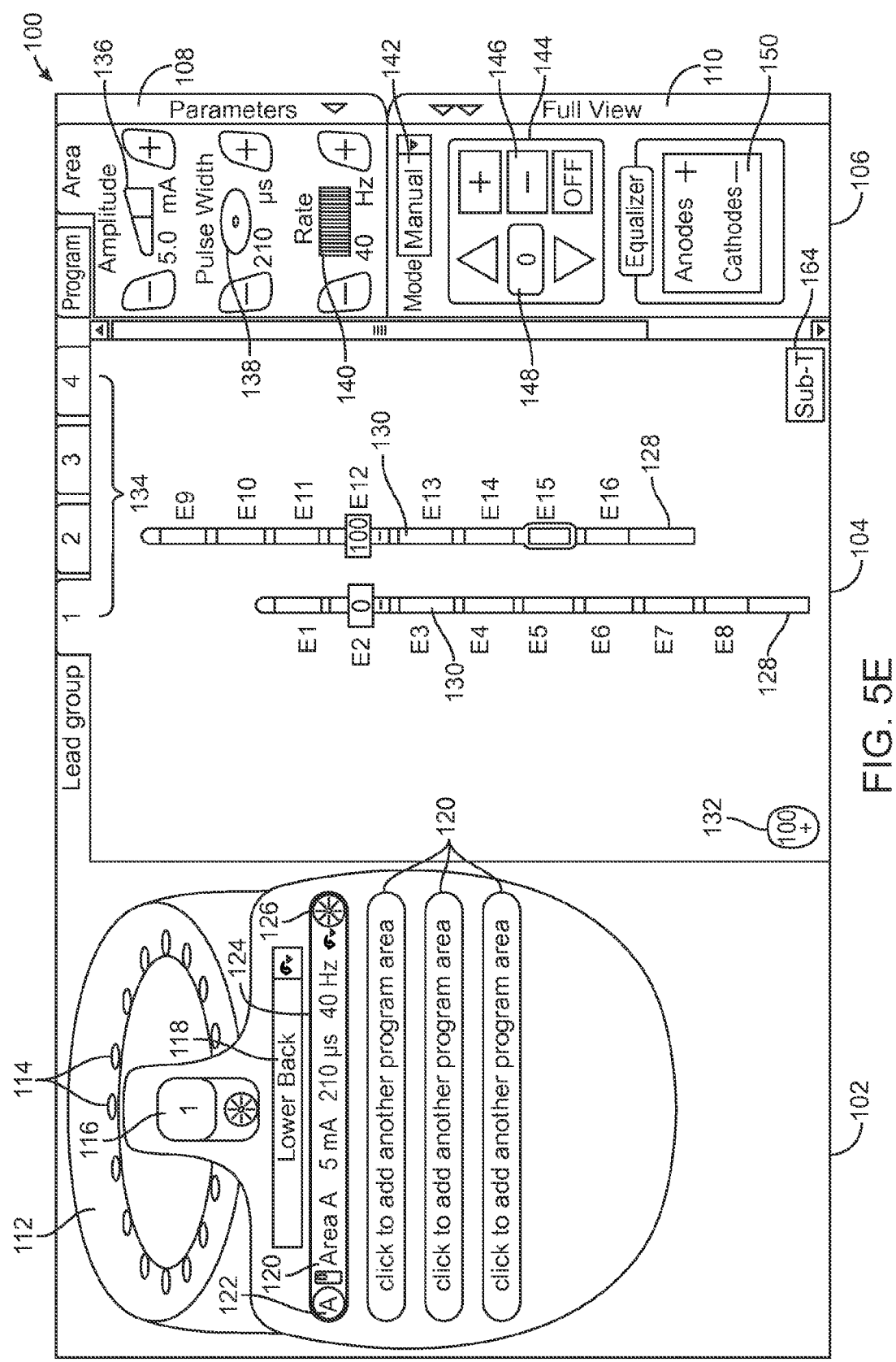

For instance, the fractionalization can be adjusted such that 75% and 25% of the cathodic current is allocated to electrodes E2 and E12, respectively, as shown in FIG. 5B. Such an adjustment would pan the electrical field locus in a rightward direction relative to the array of electrodes 26 compared to the cathodic current fractionalization depicted in FIG. 5A. When the fractionalization is adjusted such that 50% of the cathodic current is allocated to both electrodes E2 and E12, as shown in FIG. 5C, the electrical field locus is about halfway between the leads 12 corresponding to the graphic leads 130 in the lead display panel 104. The fractionalization can also be adjusted such that 25% and 75% of the cathodic current is allocated to electrodes E2 and E12, respectively, as shown in FIG. 5D. In a similar manner, the electrical field locus can be panned to the far right of the array of electrodes 26 by setting electrode E12 to 100%, as shown in FIG. 5E. The array of electrodes 26 described above is graphically depicted in the lead display panel 104 as residing on two different graphical leads 128. However, the electrodes 26 can reside on a different number of leads 12, including a single lead 12 carrying an array of electrodes 26.

As generally described above, the electrical field locus can be moved axially downward by directing the cathodic current to electrodes E3 and E13. At this second axial level, the cathodic current can initially be directed to E3 (100%). The current can be slowly shifted to E13 to laterally pan the electrical field locus across the array of electrodes 26 at the second axial level. (Not shown).

Although the graphical controls located in the amplitude/polarity area 144 can be manipulated for any of the electrodes, a dedicated graphical control for selecting the polarity and fractionalized current value can be associated with each of the electrodes, as described in U.S. Patent Publication No. 2012/0290041, entitled "Neurostimulation System with On-Effector Programmer Control," which is expressly incorporated herein by reference.

The parameters adjustment panel 106, when the manual programming mode is selected, also includes an equalization control 150 that can be actuated to automatically equalize current allocation to all electrodes of a polarity selected by respective "Anode +" and "Cathode –" icons. The ranges of pulse rates and pulse widths of the modulation parameter sets defined during the manual programming can result in either super-threshold therapy and sub-threshold therapy. For example, the lower limit of the pulse amplitude may be as low as 0.1 mA, wherein as the upper limit of the pulse amplitude may be as high as 20 mA. The lower limit of the pulse width may be as low as 2 µs, whereas the upper limit of the pulse width may be as high as 1000 µs. For example, the lower limit of the pulse rate may be as low as 1 Hz, whereas the upper limit of the pulse rate may be as high as 50 KHz. In the illustrated embodiment, a pulse amplitude of 5 mA, a pulse width of 210 µs, and a pulse rate of 40 Hz have been selected. Thus, during the manual programming mode, the selected coverage area 120 of the selected program 114 can be programmed with a modulation parameter set designed to either deliver super-threshold therapy or sub-threshold therapy to the patient.

However, for identifying the physiological midline, the modulation parameter sets are designed to deliver super-threshold therapy to elicit feedback from the patient. For example, the lower limit value of the pulse width may be 100 µs, and the upper limit of the pulse rate may be 1500 Hz.

The electronic trolling programming mode depicted in FIGS. 6A-6H is an alternative method of programming the IPG 14 using the CP 18 to steer the locus of the electrical field generated by the IPG 14. The electronic trolling programming mode allows a user to program the IPG 14 without entering the percent of current for each selected electrode 26 and whether each selected electrode 26 is an anode or a cathode. Instead, programming the IPG 14 is simplified by using a graphical locus 160 in the CP 18 interface and an array of arrows 152 to steer to actual locus of the electrical field relative to the electrodes 26, which are represented on the CP 18 interface by graphical electrodes 130. In response to displacement of the graphical locus 160 in the CP 18 interface, the CP 18 determines the fractionalization of the current between the electrodes 26 to move the locus of the electrical field to the position represented by the displaced graphical locus 160.

In one novel current steering method, described in U.S. patent application Ser. No. 12/938,282, entitled "System and Method for Mapping Arbitrary Electric Fields to Pre-existing Lead Electrodes," which is expressly incorporated herein by reference, a stimulation target in the form of a virtual pole (e.g., a virtual bipole or tripole) is defined and the stimulation parameters, including the fractionalized current values on each of the electrodes, are computationally determined in a manner that emulates these virtual poles. It can be appreciated that current steering can be implemented by moving the virtual poles about electrode array 26, such that the appropriate fractionalized current values for the electrodes are computed for each of the various positions of the virtual pole. As a result, the current steering can be implemented using an arbitrary number and arrangement of electrodes, thereby solving the afore-described problems.

The virtual bipole or tripole can be determined using a simplified virtual tripole consisting of a cathode, and an upper (or rostral) anode and lower (or caudal) electrode located on a longitudinal axis from the cathode. The virtual tripole may be defined using three values consisting of (1) location of the cathode relative to the electrodes; (2) a focus, which is the distance between the cathode and the anode(s); and (3) a percentage of current on the upper cathode. This technique is described in U.S. Provisional Patent Application Ser. No. 61/452,965, entitled "Neurostimulation System for Defining a Generalized Virtual Multipole," which is expressly incorporated herein by reference.

Alternatively, steering tables may be utilized to execute these techniques and steer the current within the electrode array, as described in U.S. patent application Ser. No. 12/614,942, entitled "System and Method for Determining Appropriate Steering Tables for Distributing Stimulation Energy Among Multiple Neurostimulation Electrodes," which is also expressly incorporated herein by reference.

As shown in FIGS. 6A-6H, the electronic trolling programming mode has been selected. In this mode, the electrodes 130 illustrated in the lead display panel 104 that were individually selectable and configurable in manual programming mode are used for display only and are not directly selectable or controllable. Instead of an amplitude/polarity area 144, the parameter selection panel 106 includes a steering array of arrows 152 that allows steering the electrical field locus up, down, left, or right relative to the electrodes 26. In the illustrated embodiment, the electrical current is steered by laterally panning an electric field locus, which is represented by the graphical locus 160, and determining the signal parameters needed for the actual electrodes 26 to emulate the graphical electrical field locus 160. In response to the panning of the graphical locus 160 via manipulation of the steering array of arrows 152, the controller/processor 80 generates a series of modulation parameter sets (with different fractionalized electrode combinations) and transmits them to the IPG 14 via the telemetry circuitry 86 for use in delivering the modulation energy to the electrode array 26 in a manner that steers the locus of the resulting electrical field relative to the electrode array 26.

Figure 6A:
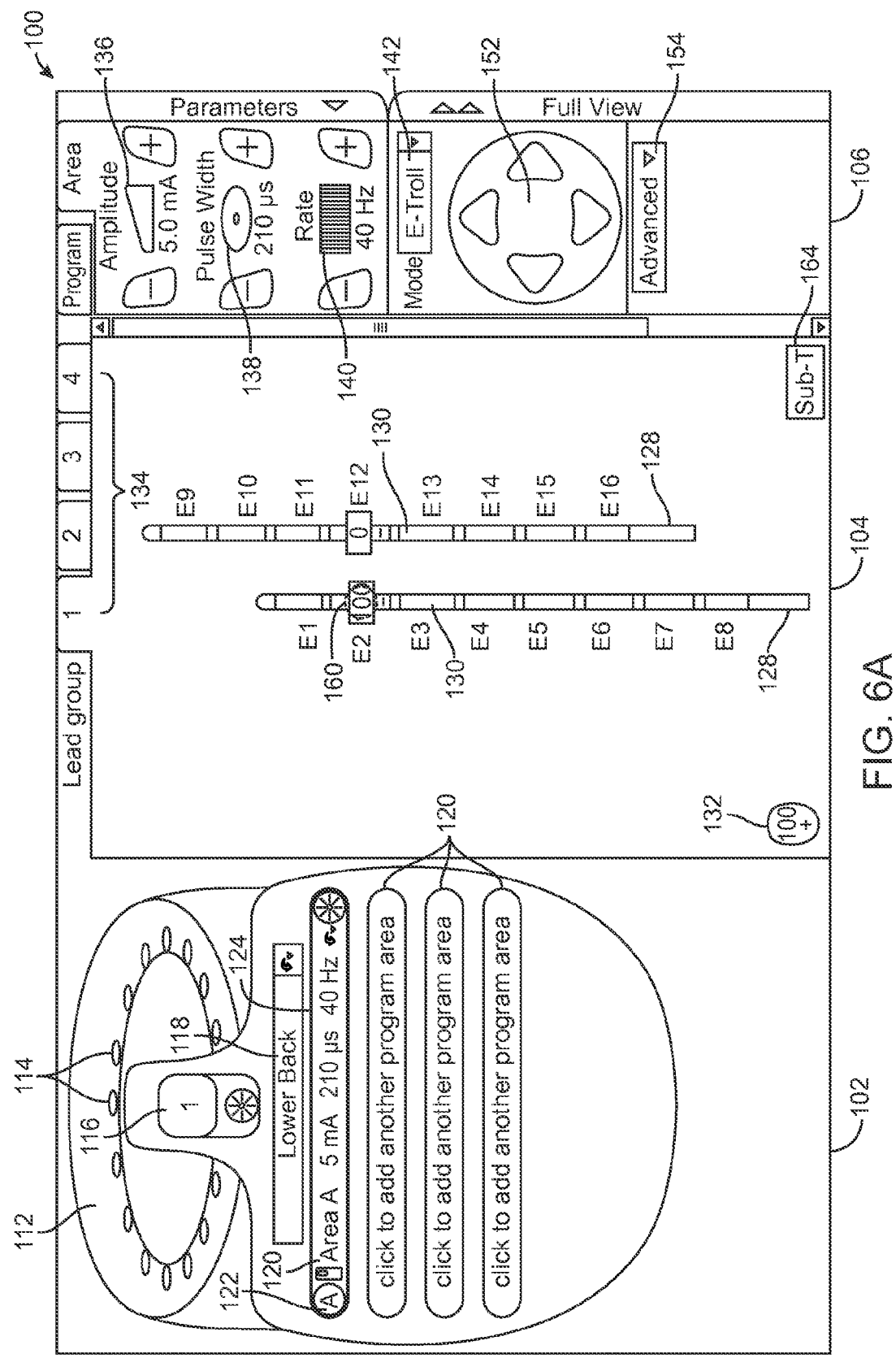
FIGS. 6A-6H are plan views of a user interface of the CP of FIG. 4 for programming the IPG of FIG. 3 in an electronic trolling programming mode.

In the embodiment illustrated in FIG. 6A, the graphical locus 160 has been panned over electrode E2 by manipulation of the steering array of arrows 152. In response, 100% of the cathodic current has been set for electrode E2, and 100% of the anodic current has been set for the graphical case 132.

Figure 6B:
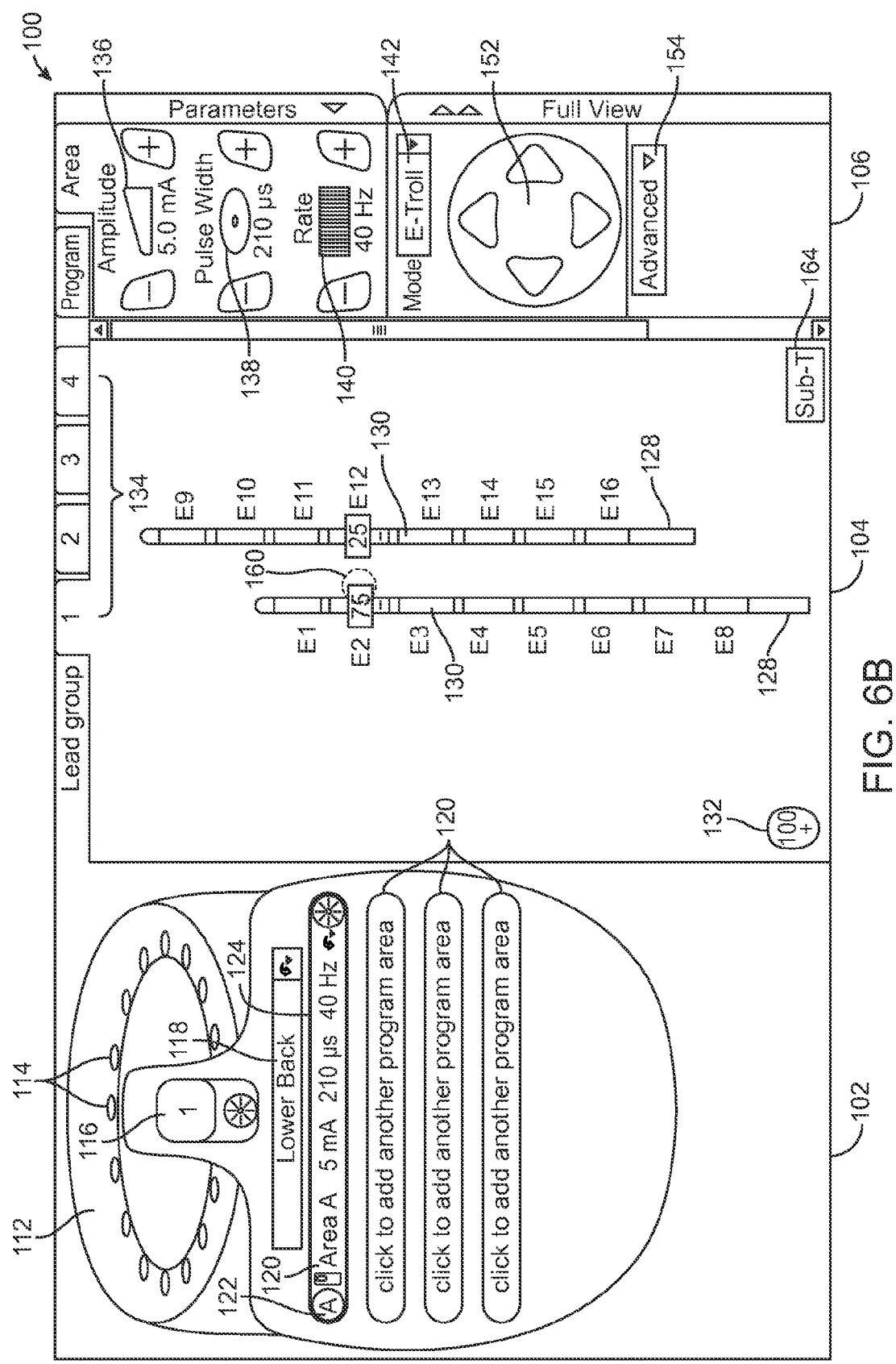

For instance, in FIG. 6B, the graphical locus 160 has been moved further to the right of the array of graphical electrodes 130 on the lead display panel 104 using the left and right arrows from the steering array of arrows 152. Using only the left and right arrows laterally pans the electrical field locus. In response to the panning of the graphical locus 160, the controller/processor 80 adjusts the fractionalization of the cathodic currents to 75% and 25% for electrodes E2 and E12, respectively.

Figure 6C:
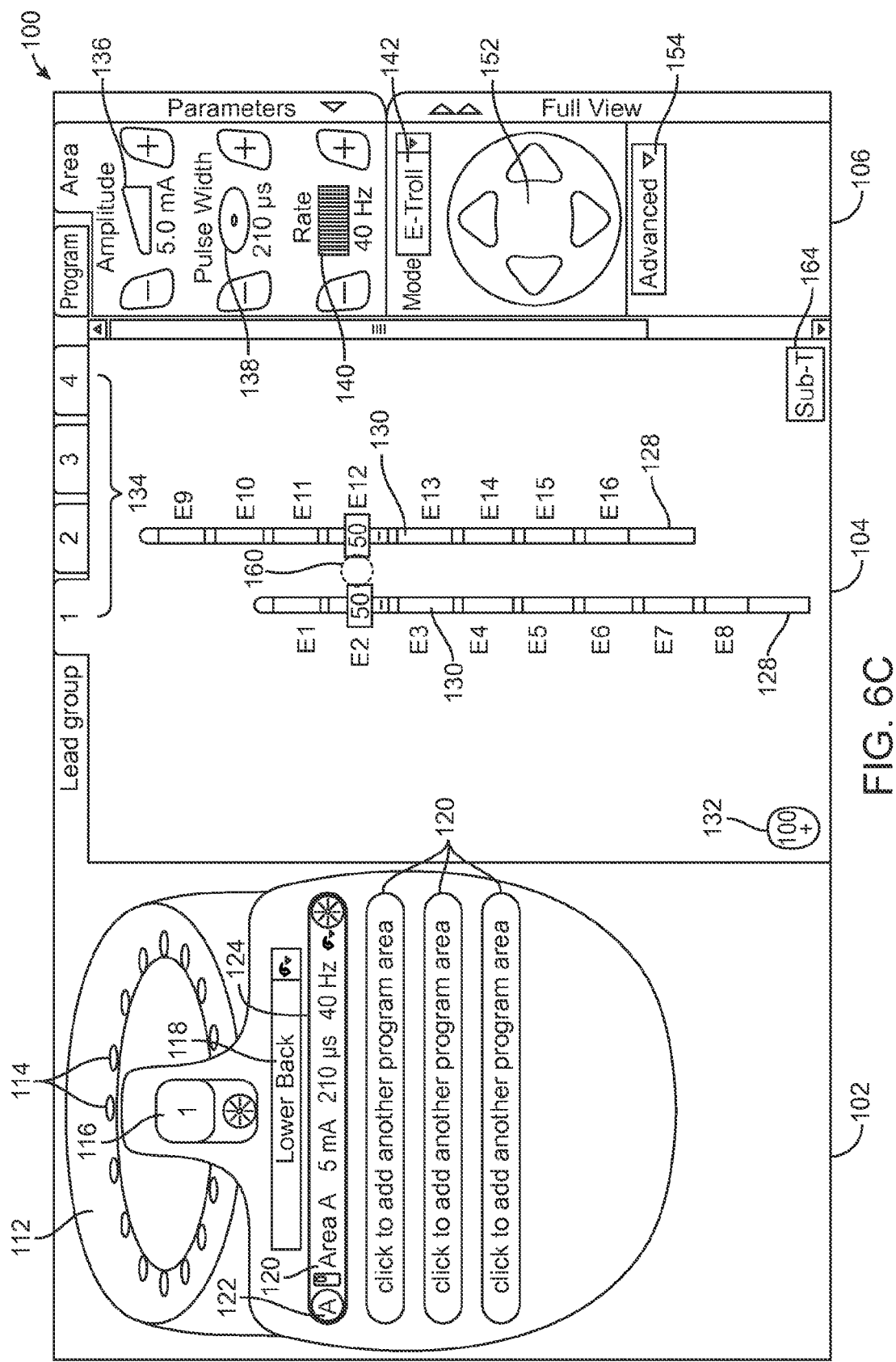
Figure 6D:
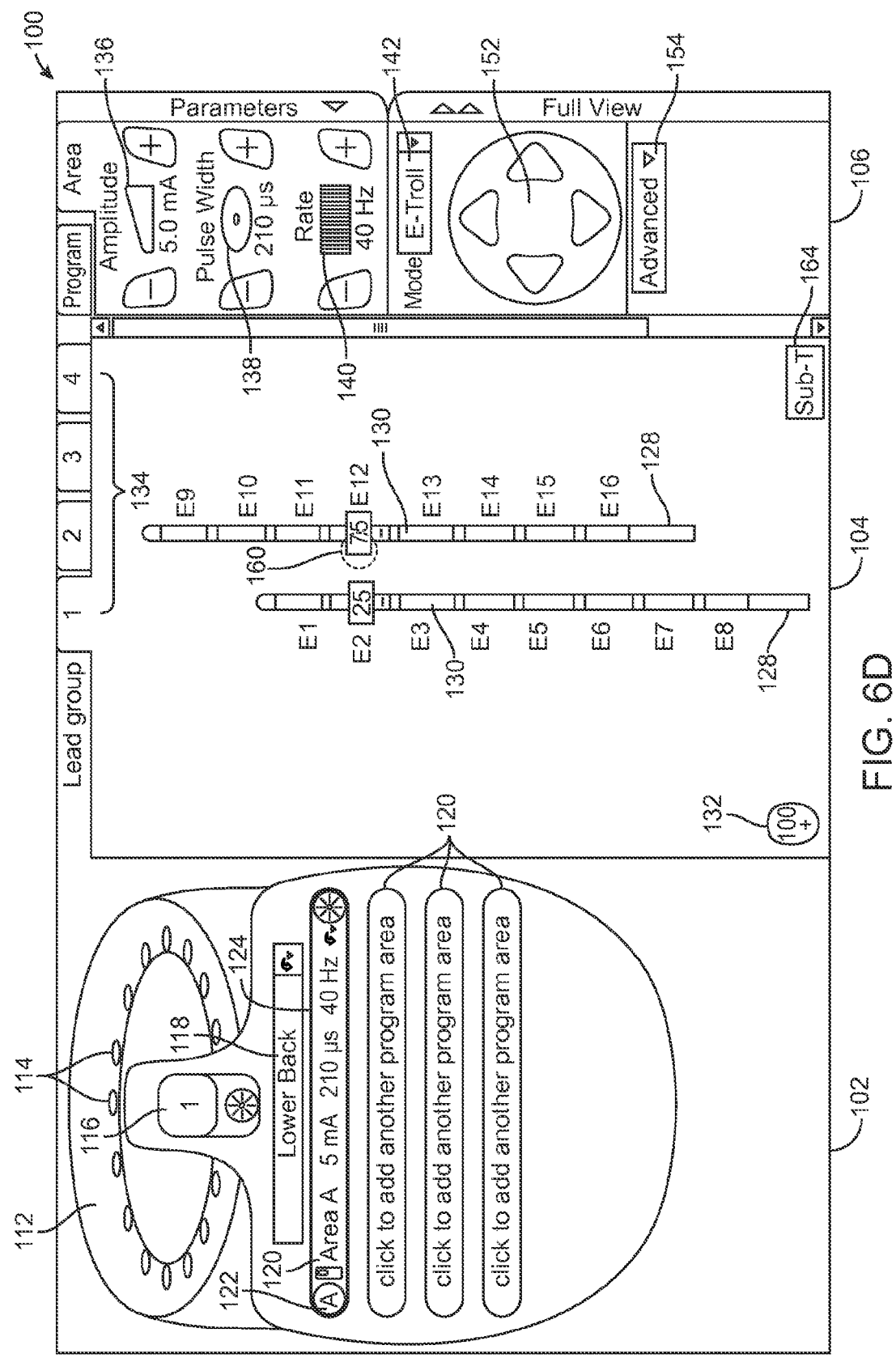
Figure 6E:
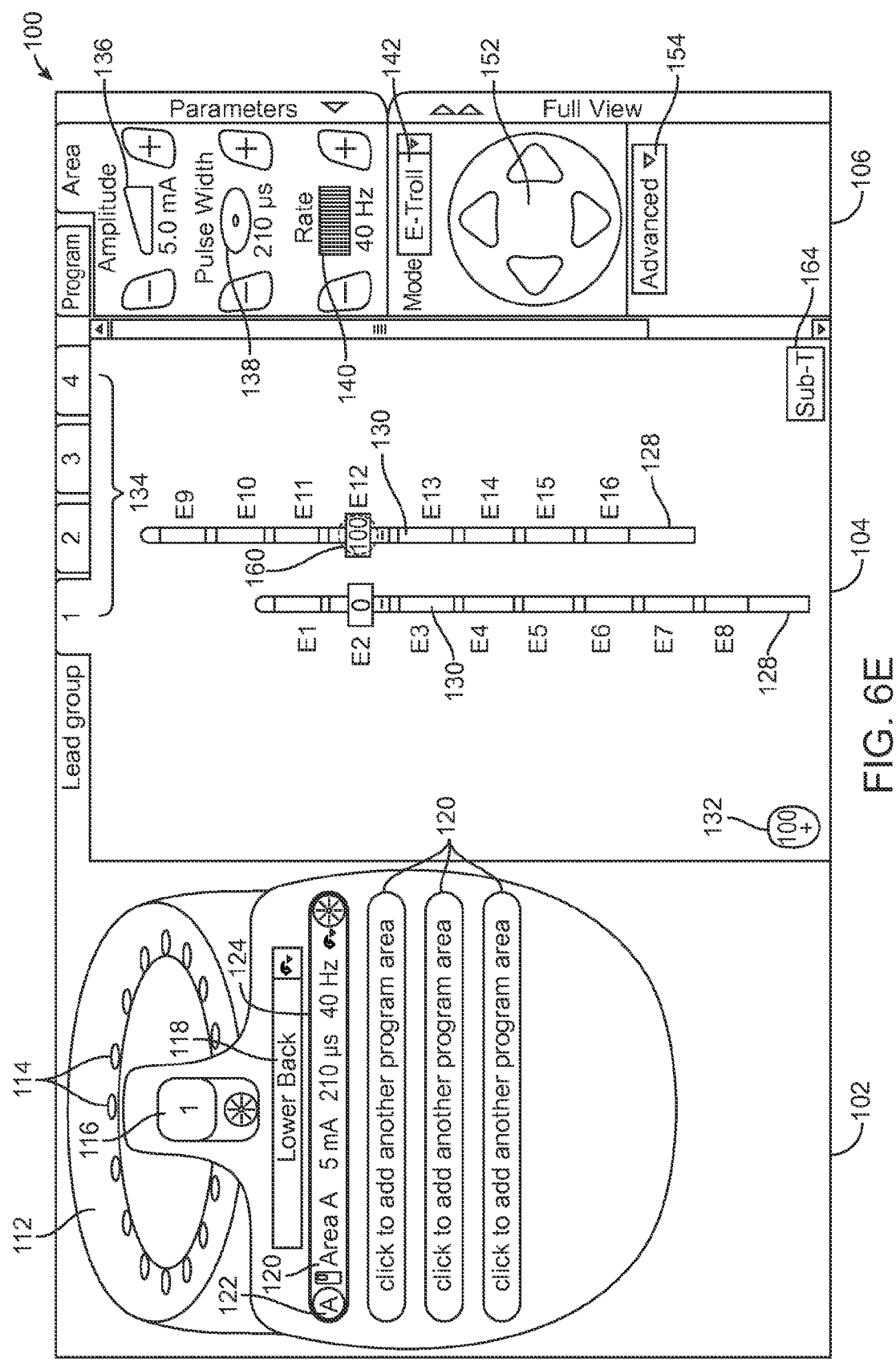

In FIG. 6C, the graphical locus 160 has been panned to the approximate center of the array of graphical electrodes 130. As a result, electrodes E2 and E12 each receive 50% of the fractionalized cathodic current. In FIG. 6D, the graphical locus 160 has been panned to the right side of the array of graphical electrodes 130, and electrodes E2 and E12 receive 25% and 75% of the fractionalized cathodic current, respectively. In FIG. 6E, the graphical locus 160 has been panned over electrode E12, and electrode E12 receives 100% of the fractionalized cathodic current.

Figure 6F:
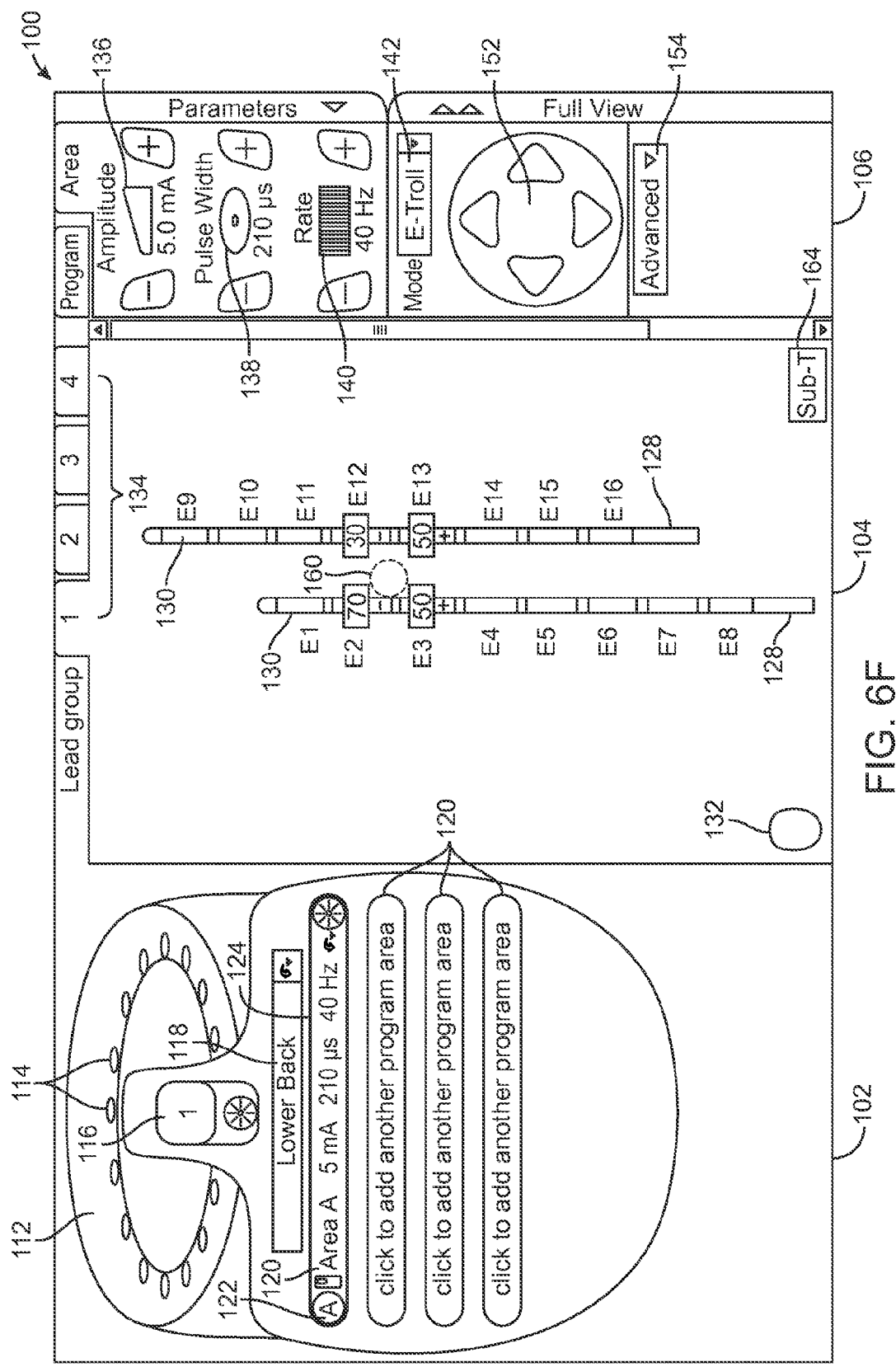

In the illustrated embodiment, the locus (represented by the graphical locus 160) used in the electronic trolling programming mode is generated using a monopole that includes a modulating cathode (i.e., cathodic modulation is providing during the electronic trolling programming mode) and an anodic IPG case 44. However, the locus can be generated using any suitable polar arrangement. For instance, FIG. 6F depicts a bipole arrangement in response to positioning the graphical locus 160 to the left side of the array of graphical electrodes 130 axially between electrodes E2 and E3. In response to the panning of the graphical locus 160, the controller/processor 80 adjusts the fractionalization of the cathodic currents to 70% and 30% for electrodes E2 and E12, respectively, and fractionalization of the anodic current to 50% for each of electrodes E3 and E13. This bipole has two cathodes (E2 and E12) and two anodes (E3 and E13).

Figure 6G:
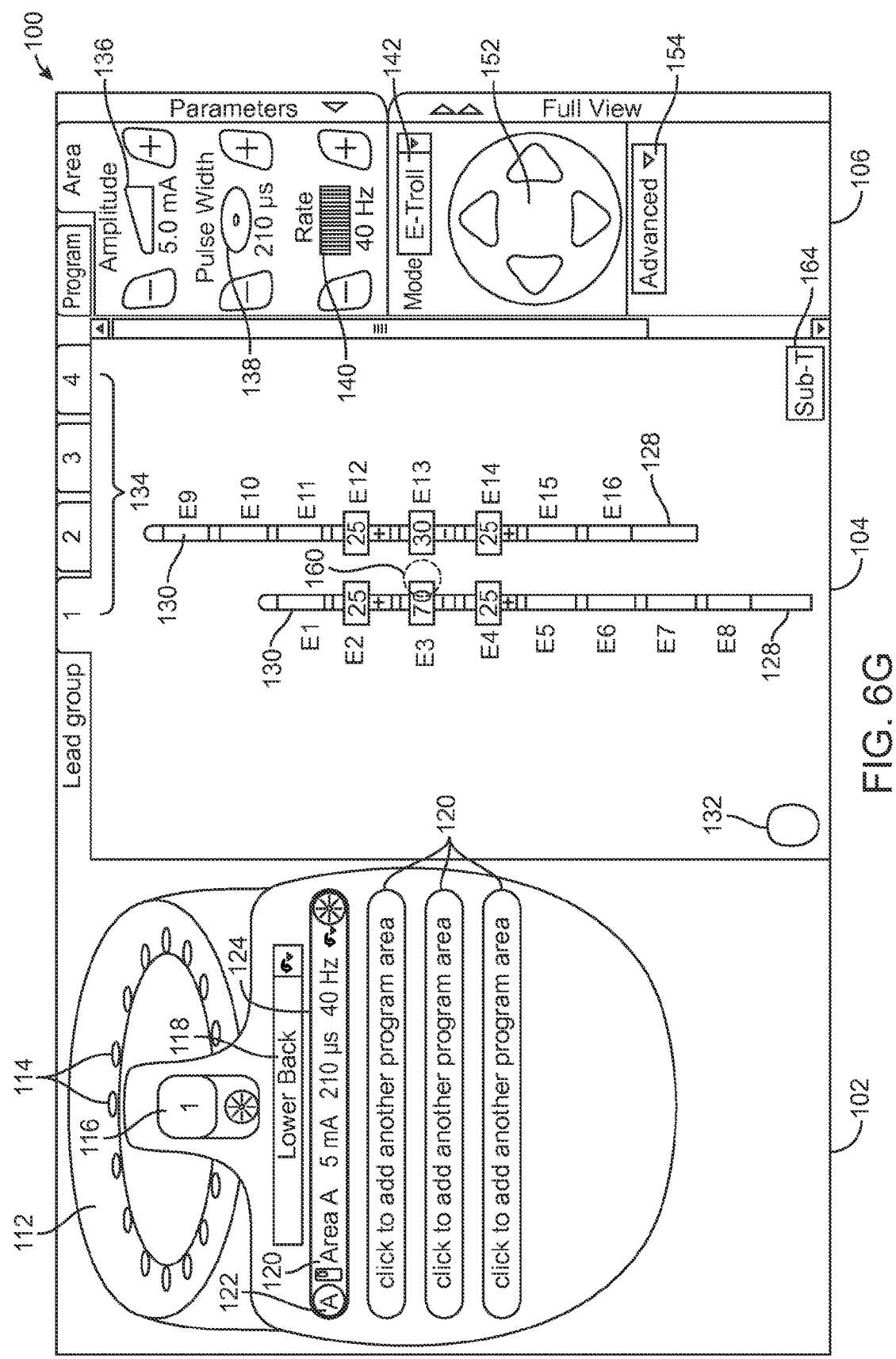

FIG. 6G depicts a tripole arrangement in response to positioning the graphical locus 160 to the left side of the array of graphical electrodes 130 axially between electrodes E2 and E3. In response to the panning of the graphical locus 160, the controller/processor 80 adjusts the fractionalization of the cathodic currents to 70% and 30% for electrodes E3 and E13, respectively, and fractionalization of the anodic current to 25% for each of electrodes E2, E4, E12, and E14. This tripole has two cathodes (E3 and E13) and four anodes (E2, E4, E12, and E14).

Figure 6H:
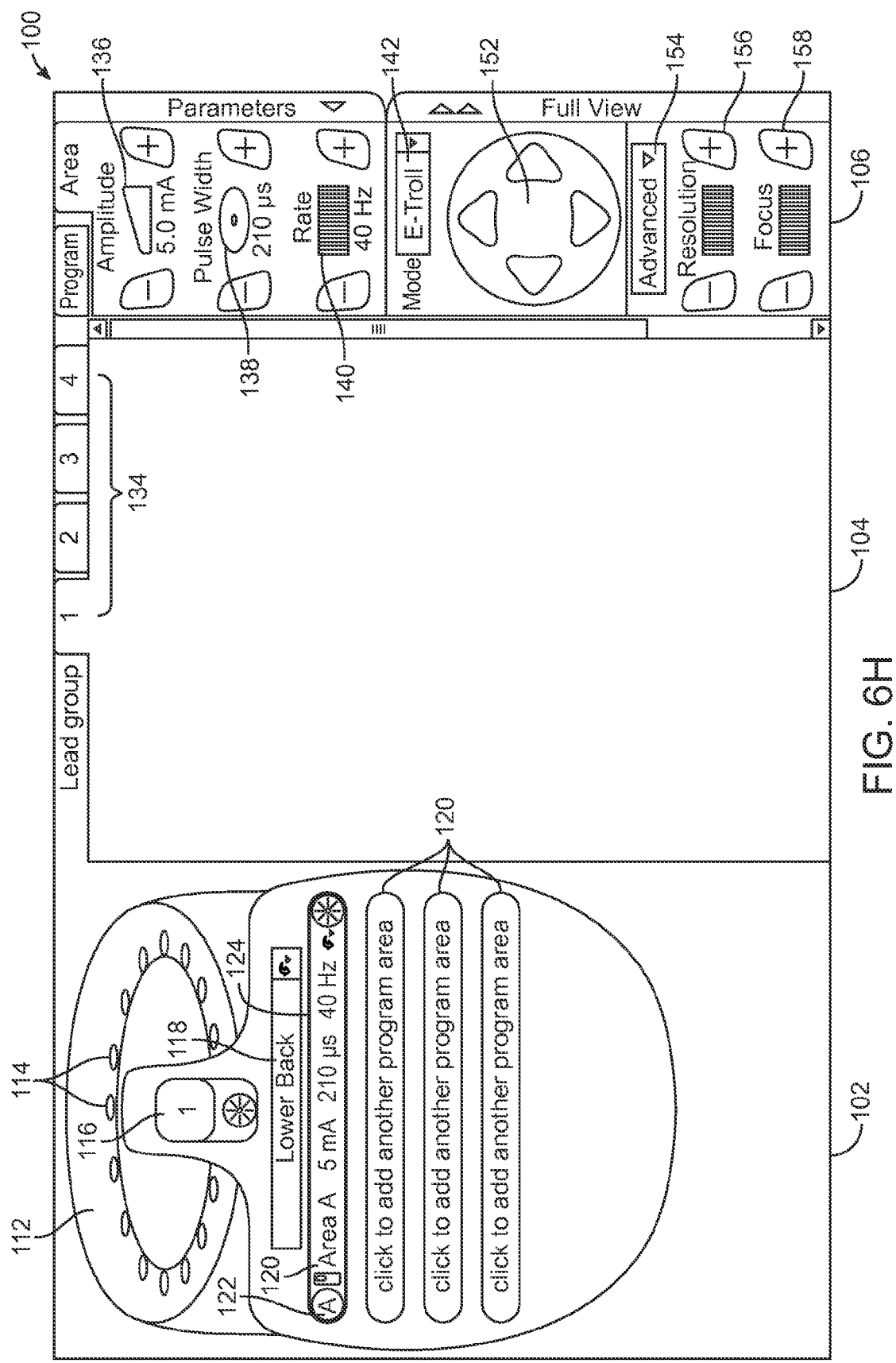

In the electronic trolling programming mode (a semi-automated mode), the parameter adjustment panel 106 includes an advanced tab 154, as shown in FIGS. 6A-6H, which when actuated, hides the lead display panel 104 and provides access to a resolution control 156 and a focus control 158, as shown in FIG. 6H. The resolution control 156 allows changing the modulation adjustment resolution. In one embodiment, three possible settings of Fine, Medium, and Coarse may be chosen. The resolution control 156 has a "+" icon and a "−" icon that can be used to adjust the resolution. The resolution control 156 also includes a display element that graphically displays the current resolution level. When the resolution is set to Fine, each change caused by use of the steering array makes less of a change to the electrode configuration than when the resolution is set to Medium or Coarse. The focus control 158 allows changing the stimulation focus by displacing the anode(s) and cathode(s) toward each other to increase the focus, or displacing the anode(s) and cathode(s) away from each other to decrease the focus. The focus control 158 has a "+" icon and a "−" icon that can be used to adjust the focus. The focus control 158 also includes a display element that graphically displays the current focus level.

The CP 18 interfaces for the manual and electronic trolling programming modes include a "Sub-T" user interface object or button 164 selectable to initiate sub-threshold stimulation (i.e., without paresthesia). When a user selects the Sub-T button, the controller/processor 80 transforms the fractionalized electrode combination (from the manual or electronic trolling programming modes) into a sub-threshold electrical field while maintaining the same locus position in the manner described in U.S. patent application Ser. No. 13/715,751, which is expressly incorporated herein by reference. For example, the ratio of the fractionalized cathodic current can be maintained while other electrical pulse parameters (amplitude, pulse width, or frequency) are modified to achieve sub-threshold stimulation.

The controller/processor 80 automatically modifies the electrical pulse parameters previously defined in the graphical controls 136-140 of the parameter adjustment panel 106 during the electronic trolling programming mode (or alternatively, the manual programming mode) to predetermined values that ensure sub-threshold modulation. However, the modified electrical pulse parameters maintain the position of the electrical field locus on the physiological midline. When the controller/processor 80 modifies the previously defined electrical pulse parameters to deliver sub-threshold modulation, the amplitude can be reduced, the pulse width can be reduced, and the frequency can be increased. For example, the pulse amplitude can be reduced from 5 mA to 2.3 mA, the pulse width can be decreased from 210 μs to 40 μs, and the pulse rate can be increased from 40 Hz to 2 KHz. In general, it is preferred that the super-threshold pulse amplitude used in the manual and electronic trolling programming modes be reduced by 30%-70% to obtain the sub-threshold pulse amplitude in order to ensure efficacious sub-threshold therapy. In general, the ranges of the pulse amplitudes, pulse rates, and pulse widths of the modified modulation parameter sets are limited to those known to result in sub-threshold therapy (e.g., not causing paresthesia). For example, the upper limit value of the pulse amplitude may be 5 mA, the upper limit value of the pulse width may be 100 μs, and the lower limit of the pulse rate may be 1500 Hz.

Thus, it can be appreciated from the foregoing that the controller/processor 80 is capable of deriving a modulation parameter set (fractionalized electrode combination, pulse amplitude, pulse width, and/or pulse rate) for sub-threshold stimulation from a modulation parameter set previously determined during the manual and electronic trolling programming modes. The electrical field that results from the delivery of the electrical energy to the electrode array 26 in accordance with the new modulation parameter set defined for sub-threshold stimulation will have a locus that is the same as the locus of the electrical field resulting from the conveyance of the electrical energy to the plurality of electrodes in accordance with the last modulation parameter set defined for the manual and electronic trolling programming modes, i.e. at the physiological midline of the patient. The electrical field locus is kept constant by keeping the same fractionalized electrode combination between the previously determined modulation parameter set and the new modulation parameter set.

Figure 7:
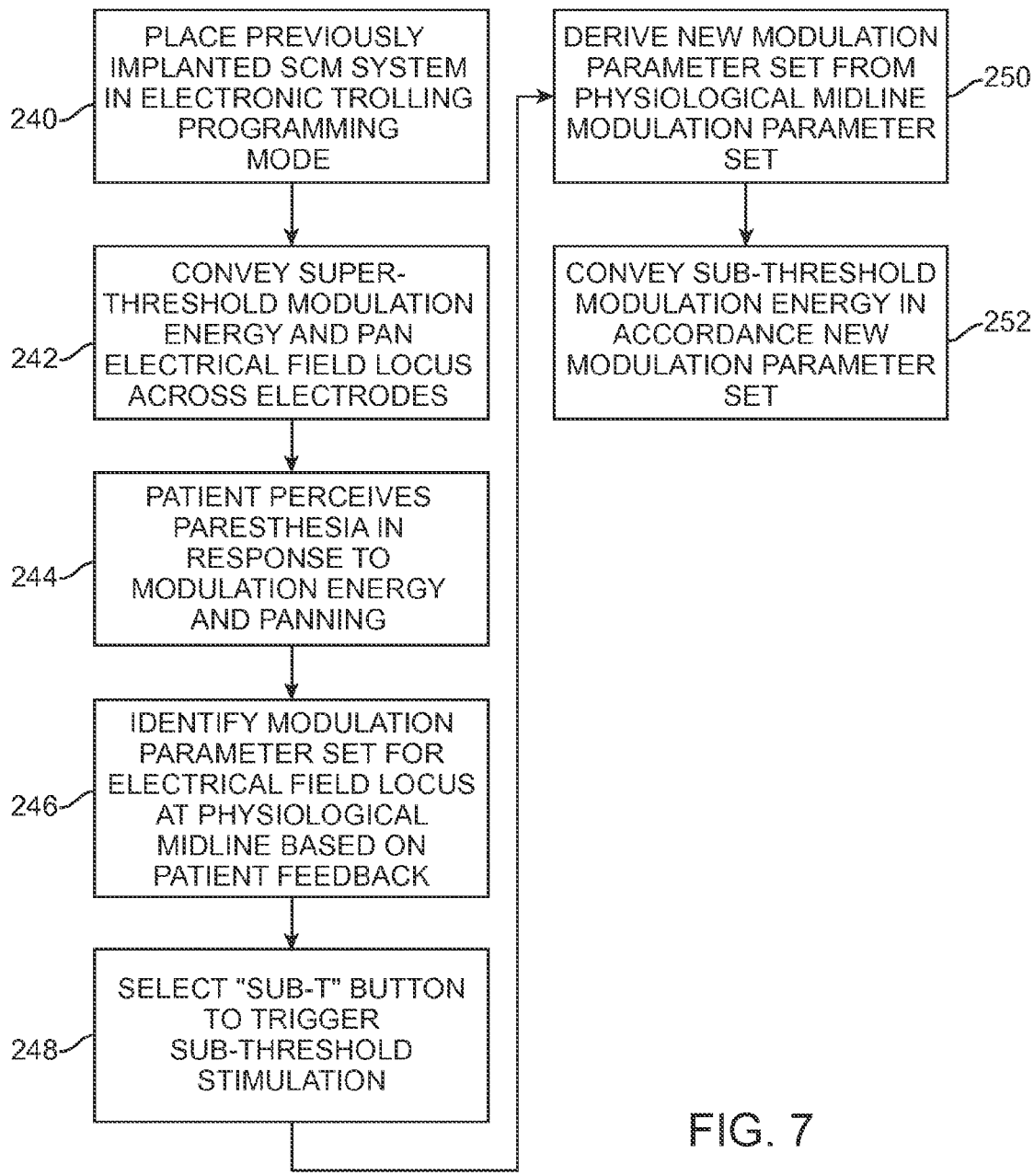
FIG. 7 a flow diagram illustrating steps for using the CP of FIG. 4 to program the IPG of FIG. 3 to provide sub-threshold therapy to a patient to treat chronic pain.

Having described the structure and function of the SCM system 10, one method of using it to identify a physiological midline of a patient and to provide sub-threshold therapy to the patient at the identified physiological midline to treat chronic pain will now be described with reference to FIG. 7. First, the electrical leads 12 and the IPG 14 are implanted in the patient. During the implantation step, care is taken to position the electrical leads 12 on either side of the anatomic midline of the patient (i.e., around the spine of the patient). Despite the current understanding that modulation therapy should generate an electrical field at the same location in the patient's body as the pain that is the target of treatment, sub-threshold modulation therapy delivered to the physiological midline of a patient may be more effective than the same therapy delivered to the location of the pain in the patient's body. However, it is difficult to immediately determine if the sub-threshold neuromodulation therapy is delivered to the physiological midline of a patient, because of the lack of paresthesia and because the physiological midline does not necessarily coincide with the anatomic midline. The remaining steps of this exemplary method address this problem by identifying the physiological midline of a patient using super-threshold stimulation before delivering sub-threshold stimulation to the physiological midline of the patient.

The SCM system 10 is placed in the electronic trolling programming mode as shown in FIGS. 6A-6E (step 240). Alternatively, this method may employ the manual programming mode as described above with reference to FIGS. 5A-5E. Then, the SCM system 10 is operated to convey electrical modulation energy to the spinal cord tissue of the patient in accordance with a series of modulation parameter sets, such that the locus of the resulting electrical field is gradually displaced in a lateral direction relative to the patient's anatomic midline from an extreme left side of the array at an axial level to the extreme right side of the array at that axial level (step 242). The electrical field locus is panned by manipulating the steering array 172 as discussed above with reference to FIGS. 6A-6E, in which the fractionalized cathodic current starts at 100% on the left side of the array of electrodes 26 at electrode E2 (see FIG. 6A). The fractionalized cathodic current is gradually shifted to the right side of the array of electrodes 26 until 100% of the cathodic current is delivered through electrode E12 (see FIG. 6E), thereby creating a series of modulation parameter sets having different fractionalized cathodic current. Each of the modulation parameter sets defines electrical pulse parameters likely to cause the patient to perceive paresthesia. For example, each of the modulation parameter sets can define a pulse rate less than 1500 Hz and/or a pulse width greater than 100 µs. The conveyed electrical modulation energy may be monopolar in nature, and may be monophasic or biphasic (with a passive charge recovery phase).

The patient perceives paresthesia in response to the conveyance of the electrical modulation energy to the tissue in accordance with the modulation parameter sets (step 244). Further, at least one of the fractionalized electrode combinations may cause the patient to perceive paresthesia of equal intensity on both sides of the patient's body (i.e., at the physiological midline). The fractionalized electrode combination that results in paresthesia of equal intensity on both sides of the patient's body (i.e., at the physiological midline) based on feedback from the patient may then be identified (step 246). Optionally, the electrical field locus is axially panned to a new axial level and steps 242-246 are repeated at the new axial level to identify the physiological midline at the new axial level.

Next, the "Sub-T" button 164 in the CP 18 user interface is selected (step 248). In response, either the CP 18 or the IPG 14 derives a new modulation parameter set is from the previously identified modulation parameter set (step 250). The new modulation parameter set defines electrical pulse parameters likely to cause the patient to not perceive paresthesia. For example, each of the modulation parameter sets can define a pulse rate greater than 1500 Hz and/or a pulse width less than 100 µs. The new (sub-threshold) modulation parameter set maintains the fractionalized electrode combination from the previously identified modulation parameter set. Therefore, the locus of the new electrical field remains at the same position (i.e., on the physiological midline) as the previous electrical field generated by the previously identified modulation parameter set.

The SCM system 10 is then operated to convey electrical modulation energy to the spinal cord tissue of the patient in accordance with new modulation parameter set to create an electrical field having a locus relative to the spinal cord tissue that is the same as the locus of the electrical field associated with the identified modulation parameter set (i.e., at the physiological midline), and without causing the patient to perceive paresthesia (step 252).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of operating an implantable neuromodulator coupled to an electrode array implanted adjacent tissue of a patient having a medical condition, comprising:
    conveying electrical modulation energy to the patient's tissue in accordance with a series of modulation parameter sets, thereby gradually displacing a locus of a resulting electrical field laterally relative to the tissue, such that a plurality of different loci of the resulting electrical field can be respectively associated with the series of modulation parameter sets;
    causing the patient to perceive paresthesia in response to the conveyance of the electrical modulation energy to the tissue in accordance with at least one of the modulation parameter sets;
    identifying one of the at least one modulation parameter sets as creating an electrical field having another locus disposed on a physiological midline of the patient based on the perceived paresthesia;
    deriving another modulation parameter set from the identified modulation parameter set;
    conveying electrical modulation energy to the patient's tissue in accordance with the other modulation parameter sets, thereby creating an electrical field having a new locus relative to the tissue that is the same as the locus of the electrical field associated with the identified modulation parameter set, and without causing the patient to perceive paresthesia.

2. The method of claim 1, wherein the medical condition affects a body region of the patient, the electrical modulation energy conveyed to the tissue in accordance with the identified modulation parameter set causes the patient to perceive the paresthesia in the body region.

3. The method of claim 1, wherein the medical condition is chronic pain.

4. The method of claim 1, wherein the identified modulation parameter set and the other modulation parameter set define different pulse rates.

5. The method of claim 4, wherein the identified modulation parameter set defines a pulse rate less than 1500 Hz, and the other modulation parameter set defines a pulse rate greater than 1500 Hz.

6. The method of claim 1, wherein the identified modulation parameter set and the other modulation parameter set define different pulse widths.

7. The method of claim 6, wherein the identified modulation parameter set defines a pulse width greater than 100 μs, and the other modulation parameter set defines a pulse width less than 100 μs.

8. The method of claim 1, wherein the identified modulation parameter set defines an electrode combination, and wherein the other modulation parameter set defines the same electrode combination.

9. The method of claim 8, wherein the electrode combination comprises a fractionalized electrode combination.

10. The method of claim 8, wherein the electrode combination comprises a multipolar electrode combination.

11. The method of claim 1, further comprising:
displacing a virtual pole relative to the electrode array; and
computing fractionalized electrode combinations that respectively emulate the displaced virtual pole, wherein the series of modulation parameter sets respectively define the fractionalized electrode combinations,
wherein the identified modulation parameter set defines a fractionalized electrode combination corresponding to one of the series of virtual poles, and
wherein the other modulation parameter set defines the same fractionalized electrode combination.

12. The method of claim 11, wherein the virtual pole is laterally displaced across the electrode array.

13. The method of claim 1, further comprising programming the neuromodulator with the other modulation parameter set.

14. The method of claim 1, wherein the neuromodulator is implanted within the patient.

15. The method of claim 1, wherein the tissue is spinal cord tissue.

16. The method of claim 1, further comprising displacing the locus of the resulting electrical field relative to the tissue in response to user input.

17. A method of providing therapy to a patient using an implantable neuromodulator implanted within the patient, comprising:
conveying electrical modulation energy to tissue of the patient to generate an electrical field having a locus relative to the tissue in a super-threshold mode, thereby causing the patient to perceive paresthesia;
laterally steering the locus of the electrical field by modifying a fractionalized electrode combination while operating the neuromodulator in the super-threshold delivery mode and receiving feedback from the patient to determine a physiological midpoint;
identifying a locus disposed on a physiological midline of the patient and a corresponding fractionalized electrode combination based on the perceived paresthesia;
switching operation of the neuromodulator to the a sub-threshold delivery mode, while maintaining corresponding fractionalized electrode combination; and
delivering electrical modulation energy to the identified locus on the physiological midline of the patient in the sub-threshold delivery mode to provide sub-threshold therapy to the patient,
wherein the neuromodulator delivers electrical modulation energy to the patient when in the sub-threshold delivery mode that provides sub-threshold therapy to the patient.

18. The method of claim 17, further comprising:
identifying another locus disposed on the physiological midline of the patient and another corresponding fractionalized electrode combination based on the perceived paresthesia; and
delivering electrical modulation energy to the other identified locus on the physiological midline of the patient in the sub-threshold delivery mode to provide sub-threshold therapy to the patient.

19. The method of claim 17; further comprising identifying a plurality of loci disposed on the physiological midline of the patient and a plurality of corresponding fractionalized electrode combination based on the perceived paresthesia;
fitting a curve to the plurality of loci disposed on the physiological midline;
switching operation of the neuromodulator to the a sub-threshold delivery mode; and
delivering electrical modulation energy to a point on the fitted curve of the patient in the sub-threshold delivery mode to provide sub-threshold therapy to the patient,
wherein the neuromodulator delivers electrical modulation energy to the patient when in the sub-threshold delivery mode that provides sub-threshold therapy to the patient.

20. The method of claim 17, wherein:
the neuromodulator delivers the electrical modulation energy at a pulse rate less than 1500 Hz when in the super-threshold delivery mode, and delivers the electrical modulation energy at a pulse rate greater than 1500 Hz when in the sub-threshold delivery mode; or
the neuromodulator delivers the electrical modulation energy at a pulse width greater than 100 us when in the super-threshold delivery mode, and delivers the electrical modulation energy at a pulse width less than 100 μs when in the sub-threshold delivery mode; or
the neuromodulator delivers the electrical modulation energy at a pulse width greater than 200 μs when in the super-threshold delivery mode, and delivers the electrical modulation energy at a pulse width less than 50 μs when in the sub-threshold delivery mode.

* * * * *